US012747301B2

(12) United States Patent
Ng et al.

(10) Patent No.: US 12,747,301 B2
(45) Date of Patent: Sep. 29, 2026

(54) USE OF LANCL1 AND ANTIBODIES THEREOF AS A DIAGNOSTIC AND THERAPEUTIC TARGET FOR THE MANAGEMENT AND TREATMENT OF CANCER

(71) Applicant: The University of Hong Kong, Hong Kong (CN)

(72) Inventors: Irene Oi Lin Lui Ng, Hong Kong (CN); Yu Man Tsui, Hong Kong (CN)

(73) Assignee: The University of Hong Kong, Hong Kong (CN)

( * ) Notice: Subject to any disclaimer, the term of this patent is extended or adjusted under 35 U.S.C. 154(b) by 593 days.

(21) Appl. No.: 18/189,528

(22) Filed: Mar. 24, 2023

(65) Prior Publication Data

US 2023/0348622 A1 Nov. 2, 2023

Related U.S. Application Data

(60) Provisional application No. 63/363,675, filed on Apr. 27, 2022.

(51) Int. Cl.
*C07K 16/40* (2006.01)
*A61P 35/00* (2006.01)
*A61K 39/00* (2006.01)

(52) U.S. Cl.
CPC .............. *C07K 16/40* (2013.01); *A61P 35/00* (2018.01); *A61K 2039/505* (2013.01)

(58) Field of Classification Search
CPC ..... C07K 16/40; C07K 2317/76; A61P 35/00; A61K 2039/505
USPC ....................................................... 424/146.1
See application file for complete search history.

(56) References Cited

PUBLICATIONS

Almagro & Fransson, Frontiers in Bioscience 2008; 13:1619-33.*
De Genst et al., Dev Comp Immunol 2006; 30:187-98.*
Yoshinaga et al., J. Biochem 2008; 143: 593-601.*
Novus Biologicals NBP1-81796 antibody (Sep. 28, 2019, pp. 1-4).*
Product datasheet of NBP1-81796 (Feb. 21, 2025, pp. 1-4).*
Althubiti, M., et al., "Characterization of novel markers of senescence and their prognostic potential in cancer," Cell Death and Disease, 2014, 5:1-10.
Yi, S.-Y., et al., "Cancer stem cells niche: A target for novel cancer therapeutics," Cancer Treatment Reviews, 2013, 39:290-296.
Visvader, J.E., et al., "Cancer stem cells in solid tumours: accumulating evidence and unresolved questions," Nature Reviews Cancer, Oct. 2008, 8:755-768.
Tirino, V., et al., "Cancer stem cells in solid tumors: an overview and new approaches for their isolation and characterization," The FASEB Journal, Jan. 2013, 27:13-24.
Sze, K.M.-F., et al., "Hepatitis B Virus—Telomerase Reverse Transcriptase Promoter Integration Harnesses Host ELF4, Resulting in Telomerase Reverse Transcriptase Gene Transcription in Hepatocellular Carcinoma," Hepatology, Jan. 2021, 73(1):23-40.
Huang, C., et al., "Developmental and Activity-Dependent Expression of LanCL1 Confers Antioxidant Activity Required for Neuronal Survival," Developmental Cell, Aug. 25, 2014, 30:479-487.
Wang, J., et al., "LanCL1 protects prostate cancer cells from oxidative stress via suppression of JNK pathway," Cell Death and Disease, 2018, 9(197):1-12.
Lee, T.K.W., et al., "CD24+ Liver Tumor-Initiating Cells Drive Self-Renewal and Tumor Initiation through STAT3-Mediated NANOG Regulation," Cell Stem Cell, Jul. 8, 2011, 9:50-63.
Ma, S., et al., "Identification and Characterization of Tumorigenic Liver Cancer Stem/Progenitor Cells," Gastroenterology, Jun. 2007, 132(7):2542-2556.
Cui, C.-P., et al., "SENP1 promotes hypoxia-induced cancer stemness by HIF-1α deSUMOylation and SENP1/HIF-1α positive feedback loop," Gut, 2017, 66:2149-2159.

* cited by examiner

*Primary Examiner* — Yan Xiao
(74) *Attorney, Agent, or Firm* — SALIWANCHIK, LLOYD & EISENSCHENK

(57) ABSTRACT

The subject invention pertains to antibodies that target LANCL1. The anti-LANCL1 antibodies can be used in methods of treating cancer, including hepatocellular carcinoma. The anti-LANCL1 antibody can be used as a therapeutic regimen for treatment or as part of a combination treatment. Further, the anti-LANCL1 antibodies may also be useful for targeting the tumor initiating cells.

3 Claims, 26 Drawing Sheets

Specification includes a Sequence Listing.

****P < 0.001

****P < 0.001

| No. of cells injected | Tumor incidence | | | | |
|---|---|---|---|---|---|
| | NTC +Vec ctrl | shLANCL #1 + Vec ctrl | shLANCL #4 + Vec ctrl | shLANCL #1 + LANCL1-O/E | shLANCL #4 + LANCL1-O/E |
| 5 x $10^5$ | 6/6 | 4/6 | 4/6 | 6/6 | 6/6 |
| 5 x $10^4$ | 6/6 | 2/6 | 2/6 | 6/6 | 6/6 |
| 5 x $10^3$ | 6/6 | 1/6 | 2/6 | 6/6 | 6/6 |
| Tumorigenic cells frequency (95% CI) | 1/1 (1/3,311-1/1) | 1/224,008 ^ (1/418,397-1/119,933) | 1/287,808 ^ (1/537,404-1/154,137) | 1/1 ^ (1/5,353-1/1) | 1/1 ^ (1/5,353-1/1) |

^ For comparing the respective groups with NTC

| No. of cells injected with PBS (1X) | Tumor incidence | | |
|---|---|---|---|
| | NTC | shLANCL1#1 | shLANCL1#4 |
| $5 \times 10^5$ | 6 / 6 | 0 / 6 | 3 / 6 |
| $5 \times 10^4$ | 5 / 6 | 0 / 6 | 0 / 6 |
| $5 \times 10^3$ | 2 / 6 | 0 / 6 | 0 / 6 |
| Tumorigenic cells frequency (95% CI) | 1/22,394 (1/54,842-1/9,144) | Infinity (Infinity-1/1,111,582) | 1/835,214 (1/2,585,864-1/269,768) |

Three independent trials; *: P<0.05; **: P<0.001

Three independent trials;
*: 0.001<P≤0.05; **: P≤0.001

Three independent trials;
*: 0.001<P≤0.05; **: P≤0.001

(A)

| | Brand (Cat. no.) | Host species | Immunogen | Isolation method | IHC | Western blot | IF and flow cytometry |
|---|---|---|---|---|---|---|---|
| 1. | Sigma-Aldrich (HPA034994) | Rabbit (polyclonal) | 1-47th aa of 399aa | Affinity isolation | Non-specific nuclear stain | OK but extra non-specific band present | OK (needs fixing the cells) |
| 2. | Abcam (ab151290) | Rabbit (polyclonal) | 104-399th aa of 399aa | Immunogen affinity-purified | Not ok (non-specific stain) | Only OK upon overexpression | Not ok |
| 3. | Abnova (H00010314-A01) | Mouse (polyclonal) | 1-58th aa of recombinant LANCL1 (399aa) with GST tag | Not stated | Not ok (non-specific stain) | OK | Not ok |
| 4. | Abnova (H00010314-M01) | Mouse (monoclonal) | 1-58th aa of recombinant LANCL1 (399aa) with GST tag | Not stated | Not tried | OK | Not tried |
| 5. | Assaypro (32098-05141) | Rabbit (FITC-conjugated) | 1-399th aa of 399aa | Not stated | N/A | N/A | OK (needs fixing the cells) |
| 6. | Novus Biologicals (NBP1-81796) | Rabbit (polyclonal) | 1-47th aa of 399aa | Immunogen affinity-purified | OK (according to manufacturer) | OK | OK (according to manufacturer) |

Fig. 6A

SEQUENCE LISTING

```
Sequence total quantity: 14
SEQ ID NO: 1            moltype = DNA  length = 54
FEATURE                 Location/Qualifiers
misc_feature            1..54
                        note = oligo (forward) sequence 1 for cloning the shRNA
                         targeting LANCL1
source                  1..54
                        mol_type = other DNA
                        organism = synthetic construct
SEQUENCE: 1
ccggtcacaa cgcttgacca atactcgagt attggtcaag cgttgtgatt tttg        54
```

```
SEQ ID NO: 2            moltype = DNA  length = 54
FEATURE                 Location/Qualifiers
misc_feature            1..54
                        note = oligo (reverse) sequence 2 for cloning the shRNA
                         targeting LANCL1
source                  1..54
                        mol_type = other DNA
                        organism = synthetic construct
SEQUENCE: 2
aattcaaaaa tcacaacgct tgaccaatac tcgagtattg gtcaagcgtt gtga        54

SEQ ID NO: 3            moltype = DNA  length = 54
FEATURE                 Location/Qualifiers
misc_feature            1..54
                        note = oligo (forward) sequence 3 for cloning the shRNA
                         targeting LANCL1
source                  1..54
                        mol_type = other DNA
                        organism = synthetic construct
SEQUENCE: 3
ccgggatgtg atctggcaat atgctcgagc atattgccag atcacatctt tttg        54

SEQ ID NO: 4            moltype = DNA  length = 54
FEATURE                 Location/Qualifiers
misc_feature            1..54
                        note = oligo (reverse) sequence 4 for cloning the shRNA
                         targeting LANCL1
source                  1..54
                        mol_type = other DNA
                        organism = synthetic construct
SEQUENCE: 4
aattcaaaaa gatgtgatct ggcaatatgc tcgagcatat tgccagatca catc        54

SEQ ID NO: 5            moltype = AA  length = 399
FEATURE                 Location/Qualifiers
source                  1..399
                        mol_type = protein
                        organism = Homo sapiens
SEQUENCE: 5
MAQRAFPNPY ADYNKSLAEG YFDAAGRLTP EFSQRLTNKI RELLQQMERG LKSADPRDGT  60
GYTGWAGIAV LYLHLYDVFG DPAYLQLAHG YVKQSLNCLT KRSITFLCGD AGPLAVAAVL  120
YHKMNNEKQA EDCITRLIHL NKIDPHAPNE MLYGRIGYIY ALLFVNKNFG VEKIPQSHIQ  180
QICETILTSG ENLARKRNFT AKSPLMYEWY QEYYVGAAHG LAGIYYYLMQ PSLQVSQGKL  240
HSLVKPSVDY VCQLKFPSGN YPPCIGDNRD LLVHWCHGAP GVIYMLIQAY KVFREEKYLC  300
DAYQCADVIW QYGLLKKGYG LCHGSAGNAY AFLTLYNLTQ DMKYLYRACK FAEWCLEYGE  360
HGCRTPDTPF SLFEGMAGTI YFLADLLVPT KARFPAFEL                         399

SEQ ID NO: 6            moltype = DNA  length = 1200
FEATURE                 Location/Qualifiers
source                  1..1200
                        mol_type = genomic DNA
                        organism = Homo sapiens
SEQUENCE: 6
atggctcaaa gggccttccc gaatccttat gctgattata acaaatccct ggccgaaggc  60
tactttgatg ctgccgggag gctgactcct gagttctcac aacgcttgac caataagatt  120
cgggagcttc ttcagcaaat ggagagaggc ctgaaatcag cagaccctcg ggatggcacc  180
ggttacactg gctgggcagg tattgctgtg ctttacttac atctttatga tgtatttggg  240
gaccctgcct acctacagtt agcacatggc tatgtaaagc aaagtctgaa ctgcttaacc  300
aagcgctcca tcaccttcct ttgtggggat gcaggccccc tggcagtggc cgctgtgcta  360
tatcacaaga tgaacaatga gaagcaggca gaagattgca tcacacggct aattcaccta  420
aataagattg atcctcatgc tccaaatgaa atgctctatg ggcgaatagg ctacatctat  480
gctcttcttt ttgtcaataa gaactttgga gtggaaaaga ttcctcaaag ccatattcag  540
cagatttgtg aaacaatttt aacctctgga gaaaacctag ctaggaagag aaacttcacg  600
gcaaagtctc cactgatgta tgaatggtac caggaatatt atgtaggggc tgctcatggc  660
ctggctggaa tttattacta cctgatgcag cccagccttc aagtgagcca agggaagtta  720
catagtttgg tcaagcccag tgtagactac gtctgccagc tgaaattccc ttctggcaat  780
taccctccat gtataggtga taatcgagat ctgcttgtcc attggtgcca tggcgcccct  840
ggggtaatct acatgctcat ccaggcctat aaggtattca gagaggaaaa gtatctctgt  900
gatgcctatc agtgtgctga tgtgatctgg caatatgggt tgctgaagaa gggatatggg  960
ctgtgccacg gttctgcagg gaatgcctat gccttcctga cactctacaa cctcacacag  1020
gacatgaagt acctgtatag ggcctgtaag tttgctgaat ggtgcttaga gtatggagaa  1080
catggatgca gaacaccaga cacccctttc tctctctttg aaggaatggc tggaacaata  1140
tatttcctgg ctgacctgct agtccccaca aaagccaggt tccctgcatt tgaactctga  1200
```

```
SEQ ID NO: 7            moltype = DNA  length = 1200
FEATURE                 Location/Qualifiers
misc_feature            1..1200
                        note = nucleotide sequence encoding non-shRNA targetable
                         mutant of LANCL1
source                  1..1200
                        mol_type = other DNA
                        organism = synthetic construct
SEQUENCE: 7
atggctcaaa gggccttccc gaatccttat gctgattata acaaatccct ggccgaaggc  60
tactttgatg ctgccgggag gctgactcct gagttcagcc agagactaac aaacaagatt  120
cgggagcttc ttcagcaaat ggagagaggc ctgaaatcag cagaccctcg ggatggcacc  180
ggttacactg gctgggcagg tattgctgtg ctttacttac atctttatga tgtatttggg  240
gaccctgcct acctacagtt agcacatggc tatgtaaagc aaagtctgaa ctgcttaacc  300
aagcgctcca tcaccttcct ttgtggggat gcaggccccc tggcagtggc cgctgtgcta  360
tatcacaaga tgaacaatga gaagcaggca gaagattgca tcacacggct aattcaccta  420
aataagattg atcctcatgc tccaaatgaa atgctctatg ggcgaatagg ctacatctat  480
gctcttcttt ttgtcaataa gaactttgga gtggaaaaga ttcctcaaag ccatattcag  540
cagatttgtg aaacaatttt aacctctgga gaaaacctag ctaggaagag aaacttcacg  600
gcaaagtctc cactgatgta tgaatggtac caggaatatt atgtaggggc tgctcatggc  660
ctggctggaa tttattacta cctgatgcag cccagccttc aagtgagcca agggaagtta  720
catagtttgg tcaagcccag tgtagactac gtctgccagc tgaaattccc ttctggcaat  780
taccctccat gtataggtga taatcgagat ctgcttgtcc attggtgcca tggcgcccct  840
ggggtaatct acatgctcat ccaggcctat aaggtattca gagaggaaaa gtatctctgt  900
gatgcctatc agtgtgctga cgtaatttgg cagtacgggt tgctgaagaa gggatatggg  960
ctgtgccacg gttctgcagg gaatgcctat gccttcctga cactctacaa cctcacacag  1020
gacatgaagt acctgtatag ggcctgtaag tttgctgaat ggtgcttaga gtatggagaa  1080
catggatgca gaacaccaga cacccctttc tctctctttg aaggaatggc tggaacaata  1140
tatttcctgg ctgacctgct agtccccaca aaagccaggt tccctgcatt tgaactctga  1200

SEQ ID NO: 8            moltype = AA  length = 405
FEATURE                 Location/Qualifiers
REGION                  1..405
                        note = amino acid sequence of the recombinant C-terminal
                         His-tagged LANCL1 protein for raising antibodies
source                  1..405
                        mol_type = protein
                        organism = synthetic construct
SEQUENCE: 8
MAQRAFPNPY ADYNKSLAEG YFDAAGRLTP EFSQRLTNKI RELLQQMERG LKSADPRDGT  60
GYTGWAGIAV LYLHLYDVFG DPAYLQLAHG YVKQSLNCLT KRSITFLCGD AGPLAVAAVL  120
YHKMNNEKQA EDCITRLIHL NKIDPHAPNE MLYGRIGYIY ALLFVNKNFG VEKIPQSHIQ  180
QICETILTSG ENLARKRNFT AKSPLMYEWY QEYYVGAAHG LAGIYYYLMQ PSLQVSQGKL  240
HSLVKPSVDY VCQLKFPSGN YPPCIGDNRD LLVHWCHGAP GVIYMLIQAY KVFREEKYLC  300
DAYQCADVIW QYGLLKKGYG LCHGSAGNAY AFLTLYNLTQ DMKYLYRACK FAEWCLEYGE  360
HGCRTPDTPF SLFEGMAGTI YFLADLLVPT KARFPAFELH HHHHH                405

SEQ ID NO: 9            moltype = DNA  length = 1218
FEATURE                 Location/Qualifiers
misc_feature            1..1218
                        note = nucleotide sequence encoding the recombinant
                         C-terminal His-tagged LANCL1 protein for raising antibodies
source                  1..1218
                        mol_type = other DNA
                        organism = synthetic construct
SEQUENCE: 9
atggctcaaa gggccttccc gaatccttat gctgattata acaaatccct ggccgaaggc  60
tactttgatg ctgccgggag gctgactcct gagttcagcc agagactaac aaacaagatt  120
cgggagcttc ttcagcaaat ggagagaggc ctgaaatcag cagaccctcg ggatggcacg  180
ggttacactg gctgggcagg tattgctgtg ctttacttac atctttatga tgtatttggg  240
gaccctgcct acctacagtt agcacatggc tatgtaaagc aaagtctgaa ctgcttaacc  300
aagcgctcca tcaccttcct ttgtggggat gcaggccccc tggcagtggc cgctgtgcta  360
tatcacaaga tgaacaatga gaagcaggca gaagattgca tcacacggct aattcaccta  420
aataagattg atcctcatgc tccaaatgaa atgctctatg ggcgaatagg ctacatctat  480
gctcttcttt ttgtcaataa gaactttgga gtggaaaaga ttcctcaaag ccatattcag  540
cagatttgtg aaacaatttt aacctctgga gaaaacctag ctaggaagag aaacttcacg  600
gcaaagtctc cactgatgta tgaatggtac caggaatatt atgtaggggc tgctcatggc  660
ctggctggaa tttattacta cctgatgcag cccagccttc aagtgagcca agggaagtta  720
catagtttgg tcaagcccag tgtagactac gtctgccagc tgaaattccc ttctggcaat  780
taccctccat gtataggtga taatcgagat ctgcttgtcc attggtgcca tggcgcccct  840
ggggtaatct acatgctcat ccaggcctat aaggtattca gagaggaaaa gtatctctgt  900
gatgcctatc agtgtgctga cgtaatttgg cagtacgggt tgctgaagaa gggatatggg  960
ctgtgccacg gttctgcagg gaatgcctat gccttcctga cactctacaa cctcacacag  1020
gacatgaagt acctgtatag ggcctgtaag tttgctgaat ggtgcttaga gtatggagaa  1080
catggatgca gaacaccaga cacccctttc tctctctttg aaggaatggc tggaacaata  1140
tatttcctgg ctgacctgct agtccccaca aaagccaggt tccctgcatt tgaactccat  1200
catcaccatc accactga                                              1218
```

-continued

```
SEQ ID NO: 10          moltype = AA  length = 268
FEATURE                Location/Qualifiers
REGION                 1..268
                       note = amino acid sequence of the recombinant N-terminal
                        GST-tagged LANCL1 protein 1-42amino acid region for
                        raising antibodies
source                 1..268
                       mol_type = protein
                       organism = synthetic construct
SEQUENCE: 10
MSPILGYWKI KGLVQPTRLL LEYLEEKYEE HLYERDEGDK WRNKKFELGL EFPNLPYYID  60
GDVKLTQSMA IIRYIADKHN MLGGCPKERA EISMLEGAVL DIRYGVSRIA YSKDFETLKV  120
DFLSKLPEML KMFEDRLCHK TYLNGDHVTH PDFMLYDALD VVLYMDPMCL DAFPKLVCFK  180
KRIEAIPQID KYLKSSKYIA WPLQGWQATF GGGDHPPKSD LVPRGSMAQR AFPNPYADYN  240
KSLAEGYFDA AGRLTPEFSQ RLTNKIRE                                    268

SEQ ID NO: 11          moltype = DNA  length = 807
FEATURE                Location/Qualifiers
misc_feature           1..807
                       note = nucleotide sequence encoding the recombinant
                        N-terminal GST-tagged LANCL1 protein 1-42amino acid region
                        for raising antibodies
source                 1..807
                       mol_type = other DNA
                       organism = synthetic construct
SEQUENCE: 11
atgtccccta tactaggtta ttggaaaatt aagggccttg tgcaacccac tcgacttctt  60
ttggaatatc ttgaagaaaa atatgaagag catttgtatg agcgcgatga aggtgataaa  120
tggcgaaaca aaaagtttga attgggtttg gagtttccca atcttcctta ttatattgat  180
ggtgatgtta aattaacaca gtctatggcc atcatacgtt atatagctga caagcacaac  240
atgttgggtg gttgtccaaa agagcgtgca gagatttcaa tgcttgaagg agcggttttg  300
gatattagat acggtgtttc gagaattgca tatagtaaag actttgaaac tctcaaagtt  360
gattttctta gcaagctacc tgaaatgctg aaaatgttcg aagatcgttt atgtcataaa  420
acatatttaa atggtgatca tgtaacccat cctgacttca tgttgtatga cgctcttgat  480
gttgttttat acatggaccc aatgtgcctg gatgcgttcc caaaattagt ttgttttaaa  540
aaacgtattg aagctatccc acaaattgat aagtacttga aatccagcaa gtatatagca  600
tggcctttgc agggctggca agccacgttt ggtggtggcg accatcctcc aaaatcggat  660
ctggttccgc gtggatccat ggctcaaagg gccttcccga atccttatgc tgattataac  720
aaatccctgg ccgaaggcta ctttgatgct gccgggaggc tgactcctga gttcagccag  780
agactgacca ataagattcg ggagtag                                     807

SEQ ID NO: 12          moltype = AA  length = 47
FEATURE                Location/Qualifiers
REGION                 1..47
                       note = amino acid sequence for the 1-47amino acid peptide
                        that was targeted by antibody manufactured by Novus
                        Biologicals (NBP1-81796)
source                 1..47
                       mol_type = protein
                       organism = synthetic construct
SEQUENCE: 12
MAQRAFPNPY ADYNKSLAEG YFDAAGRLTP EFSQRLTNKI RELLQQM               47

SEQ ID NO: 13          moltype = AA  length = 58
FEATURE                Location/Qualifiers
REGION                 1..58
                       note = amino acid sequence for the 1-58amino acid peptide
                        that was targeted by antibody manufactured by Abnova
                        (H00010314-A01)
source                 1..58
                       mol_type = protein
                       organism = synthetic construct
SEQUENCE: 13
MAQRAFPNPY ADYNKSLAEG YFDAAGRLTP EFSQRLTNKI RELLQQMERG LKSADPRD    58

SEQ ID NO: 14          moltype = AA  length = 47
FEATURE                Location/Qualifiers
source                 1..47
                       mol_type = protein
                       organism = synthetic construct
SEQUENCE: 14
MAQRAFPNPY ADYNKSLAEG YFDAAGRLTP EFSQRLTNKI RELLQQM               47
```

USE OF LANCL1 AND ANTIBODIES THEREOF AS A DIAGNOSTIC AND THERAPEUTIC TARGET FOR THE MANAGEMENT AND TREATMENT OF CANCER

CROSS-REFERENCE TO RELATED APPLICATION

This application claims the benefit of U.S. Provisional Application Ser. No. 63/363,675, filed Apr. 27, 2022, which is hereby incorporated by reference in its entirety including any tables, figures, or drawings.

BACKGROUND OF THE INVENTION

Liver cancer (hepatocellular carcinoma, HCC) is one of the most prevalent and killing cancers worldwide. It is the second and third leading cause of cancer deaths in China and Hong Kong, respectively. The 5-year survival rate of HCC patients, even after surgical removal of the cancer, is only ~20%. The median survival rates of patients with inoperable HCC are only in weeks. Its high mortality rate is attributable to its aggressive behavior and lack of promising curative therapy. New treatment modalities for this cancer are much awaited. In this regard, identification of critical molecular targets will be pivotal for new treatment development.

Liver tumor initiating cells (TICs) are self-renewing subpopulations in HCC contributing to initiation of tumor and the culprit for treatment resistance (1-3). They are marked by different cell-surface markers which are functional and can activate downstream cell signaling to exert their effects. It is strategic to block these TIC markers to suppress their signaling pathways to suppress tumor growth.

Currently, several TIC markers have been identified in HCC. However, some of these markers have been demonstrated to have limitations in translational applications. One reason is that some of these markers have low expression in terms of low percentages of positive cells in HCC tumors or only few patients' samples having detectable expression. Also, some markers are detectable not only in patients' HCC tumors but also at significantly high levels in non-tumorous liver tissues. The understanding of liver TIC is still insufficient and the relatively small number of liver TIC-specific markers identified hinders the development of therapeutic applications against liver TICs in cancer therapy.

Therefore, there is an urgent need to identify new functional liver TIC markers, with comprehensive characterization of their structural domains, functional characterization, and potential therapeutic targeting for HCC.

BRIEF SUMMARY OF THE INVENTION

The subject invention pertains to antibodies that target LANCL1. In certain embodiments, the anti-LANCL1 antibodies can be used in methods of treating HCC by, for example, eliminating liver TICs. In certain embodiments, an anti-LANCL1 antibody can be used as a therapeutic regimen for cancer treatment or as part of a combination treatment such as immunotherapy, chemotherapy and radiotherapy regimens, which can enhance the survival of liver cancer patients. In certain embodiments, the anti-LANCL1 antibodies can also be useful for targeting the TICs in other cancers.

BRIEF DESCRIPTION OF THE DRAWINGS

FIG. 1A. Strategy and workflow for screening cell surface functional targets in HCC cells. FIGS. 1I-1R Flow cytometry for LANCL1 expression in PLC/PRF/5 cells with respective KD and overexpression of LANCL1 protein by using Sigma-Aldrich antibody (HPA034994) that binds to the N-terminal first 47aa region upon cell fixation by 4% paraformaldehyde.

FIGS. 2A-2B Rescue of LANCL1 by overexpressing the non-shRNA targetable variant of LANCL1 reversed the inhibition of sh-LANCL1 on sphere forming ability of PLC/PRF/5 and MHCC-97L cells. FIG. 2C Rescue of LANCL1 by overexpressing the non-shRNA targetable variant of LANCL1 reversed the inhibition of sh-LANCL1 on tumorigenicity in PLC/PRF/5 cell line. FIG. 2D Stable knockdown of LANCL1 in MHCC-97L cell line suppressed tumorigenicity. FIG. 2E Stable LANCL1 knockdown suppressed the expression of certain sternness-related genes in PLC/PRF/5 cells. FIG. 2F Stable LANCL1 knockdown sensitized PLC/PRF/5 cells to cisplatin and 5-fluoruracil (5-FU) chemo-drug treatment.

FIGS. 3A-3I LANCL1 reduces ROS level in HCC cells to promote sphere formation and tumorigenicity. FIGS. 3A-3B LANCL1 KD enhances ROS level, which is reversed by anti-oxidant NAC and aggravated by oxidizing reagent TBHP in both PLC/PRF/5 and MHCC-97L cell lines. FIGS. 3C-3D LANCL1 KD enhances ROS level, which is reversed by anti-oxidant GSH and aggravated by oxidizing reagent TBHP in both PLC/PRF/5 and MHCC-97L cell lines. FIGS. 3E-3F Rescue of LANCL1 by overexpressing the non-shRNA targetable variant of LANCL1 suppressed the ROS increase originally promoted by LANCL1 KD in both PLC/PRF/5 and MHCC-97L cell lines. FIGS. 3G-3H Antioxidants reverse the inhibitory effect of shLANCL1 on sphere formation of both PLC/PRF/5 and MHCC-97L cell lines. FIG. 3I Administration of anti-oxidants NAC and GSH suppressed the promoting effects by stable LANCL1 knockdown on ROS level in PLC/PRF/5 xenograft in vivo as assayed by H2DCFDA dye in flow cytometry.

FIG. 4A Immunofluorescence for different mutants of LANCL1 with insertion of Flag tag at different positions of the proteins indicated transmembrane region. FIG. 4B Location of Flag tags of different mutants of LANCL1 protein on cell membrane. The transmembrane region is postulated to be between 100th and 150th amino acids of the protein.

FIGS. 6A-6D Testing antibodies specifically against the N-terminal of the LANCL1 protein in sphere formation of HCC cells for exploring the translational application of the antibodies in management and treatment of HCC. FIG. 6A Summary of LANCL1 antibodies currently commercially available. FIG. 6B Anti-LANCL1 antibody by Novus Biologicals (NBP1-81796) significantly suppressed sphere formation of PLC/PRF/5 cells. FIG. 6C Anti-LANCL1 antibody by Sigma-Aldrich antibody (HPA034994) significantly suppressed sphere formation of PLC/PRF/5 cells. FIG. 6D Anti-LANCL1 antibody by Abnova (H00010314-A01) significantly suppressed sphere formation of PLC/PRF/5 cells.

BRIEF DESCRIPTION OF THE SEQUENCES

Figure 1A:
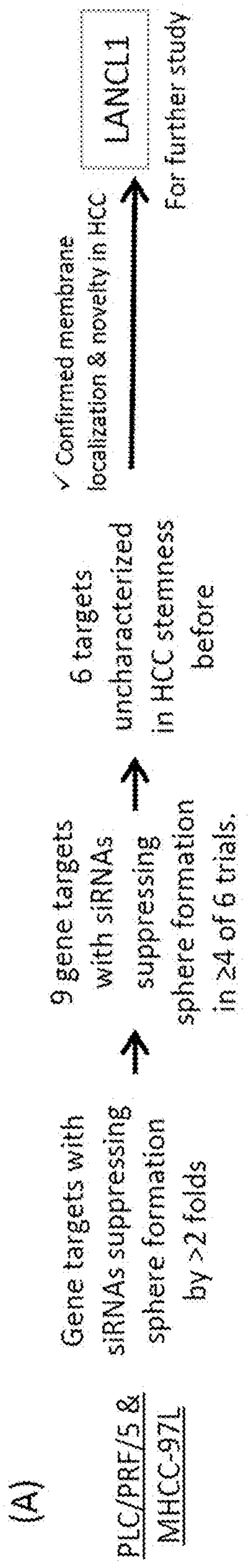
FIGS. 1A-1R Identification of potential liver TIC surface markers.

SEQ ID NO: 1: oligo (forward) sequence 1 for cloning the shRNA targeting LANCL1

SEQ ID NO: 2: oligo (reverse) sequence 2 for cloning the shRNA targeting LANCL1

SEQ ID NO: 3: oligo (forward) sequence 3 for cloning the shRNA targeting LANCL1

SEQ ID NO: 4: oligo (reverse) sequence 4 for cloning the shRNA targeting LANCL1

SEQ ID NO: 5: LANCL1 amino acid sequence

SEQ ID NO: 6: nucleotide sequence encoding LANCL1

SEQ ID NO: 7: nucleotide sequence encoding non-shRNA targetable mutant of LANCL1

SEQ ID NO: 8: amino acid sequence of the recombinant C-terminal His-tagged LANCL1 protein for raising antibodies

SEQ ID NO: 9: nucleotide sequence encoding the recombinant C-terminal His-tagged LANCL1 protein for raising antibodies SEQ ID NO: 10: amino acid sequence of the recombinant N-terminal GST-tagged LANCL1 protein 1-42amino acid region for raising antibodies SEQ ID NO: 11: nucleotide sequence encoding the recombinant N-terminal GST-tagged LANCL1 protein 1-42amino acid region for raising antibodies SEQ ID NO: 12: amino acid sequence for the 1-47 amino acid peptide that was targeted by antibody manufactured by Novus Biologicals (NBP1-81796)

SEQ ID NO: 13: amino acid sequence for the 1-58 amino acid peptide that was targeted by antibody manufactured by Abnova (H00010314-A01)

SEQ ID NO: 14: amino acid sequence for the 1-47 amino acid peptide that was targeted by antibody manufactured by Sigma-Aldrich (HPA034994)

DETAILED DISCLOSURE OF THE INVENTION

Selected Definitions

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising". The transitional terms/phrases (and any grammatical variations thereof) "comprising", "comprises", "comprise", "consisting essentially of", "consists essentially of", "consisting" and "consists" can be used interchangeably.

The phrases "consisting essentially of" or "consists essentially of" indicate that the claim encompasses embodiments containing the specified materials or steps and those that do not materially affect the basic and novel characteristic(s) of the claim.

The term "about" means within an acceptable error range for the particular value as determined by one of ordinary skill in the art, which depends in part on how the value is measured, i.e., the limitations of the measurement system. In the context of compositions containing amounts of ingredients where the terms "about" is used, these compositions contain the stated amount of the ingredient with a variation (error range) of 0-10% around the value (X±10%). In other contexts the term "about" is provides a variation (error range) of 0-10% around a given value (X±10%). As is apparent, this variation represents a range that is up to 10% above or below a given value, for example, X±1%, X±2%, X±3%, X±4%, X±5%, X±6%, X±7%, X±8%, X 9%, or X±10%.

In the present disclosure, ranges are stated in shorthand to avoid having to set out at length and describe each and every value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0, etc. Values having at least two significant digits within a range are envisioned, for example, a range of 5-10 indicates all the values between 5.0 and 10.0 as well as between 5.00 and 10.00 including the terminal values. When ranges are used herein, combinations and subcombinations of ranges (e.g., subranges within the disclosed range) and specific embodiments therein are explicitly included.

As used herein, the term "subject" refers to an animal, needing or desiring delivery of the benefits provided by a therapeutic composition. The animal may be for example, humans, pigs, horses, goats, cats, mice, rats, dogs, apes, fish, chimpanzees, orangutans, guinea pigs, hamsters, cows, sheep, birds, chickens, as well as any other vertebrate or invertebrate. These benefits can include, but are not limited to, the treatment of a health condition, disease or disorder; prevention of a health condition, disease or disorder; immune health; enhancement of the function of enamel, an organ, tissue, or system in the body. The preferred subject in the context of this invention is a human. The subject can be of any age or stage of development, including infant, toddler, adolescent, teenager, adult, or senior.

As used herein, the terms "therapeutically-effective amount," "therapeutically-effective dose," "effective amount," and "effective dose" are used to refer to an amount or dose of an antibody or composition that, when administered to a subject, is capable of treating or improving a condition, disease, or disorder in a subject or that is capable of providing enhancement in health or function to an organ, tissue, or body system. In other words, when administered to a subject, the amount is "therapeutically effective." The actual amount will vary depending on a number of factors including, but not limited to, the particular condition, disease, or disorder being treated or improved; the severity of the condition; the particular organ, tissue, or body system of which enhancement in health or function is desired; the weight, height, age, and health of the patient; and the route of administration.

As used herein, the term "treatment" refers to eradicating, reducing, ameliorating, or reversing a sign or symptom of a health condition, disease or disorder to any extent, and includes, but does not require, a complete cure of the condition, disease, or disorder. Treating can be curing, improving, or partially ameliorating a disorder. "Treatment" can also include improving or enhancing a condition or characteristic, for example, bringing the function of a particular system in the body to a heightened state of health or homeostasis.

As used herein, "preventing" a health condition, disease, or disorder refers to avoiding, delaying, forestalling, or minimizing the onset of a particular sign or symptom of the condition, disease, or disorder. Prevention can, but is not required, to be absolute or complete; meaning, the sign or symptom may still develop at a later time. Prevention can include reducing the severity of the onset of such a condition, disease, or disorder, and/or inhibiting the progression of the condition, disease, or disorder to a more severe condition, disease, or disorder.

By "reduces" is meant a negative alteration of at least 1%, 5%, 10%, 25%, 50%, 75%, or 100%.

By "increases" is meant as a positive alteration of at least 1%, 5%, 10%, 25%, 50%, 75%, or 100%.

In some embodiments of the invention, the method comprises administration of multiple doses of the antibody compositions of the subject invention. The method may comprise administration of 1, 2, 3, 4, 5, 6, 7, 8, 9, 10, 15, 20, 25, 30, 35, 40, or more therapeutically effective doses of a composition comprising the antibodies of the subject invention as described herein. In some embodiments, doses are administered over the course of 1 day, 2 days, 3 days, 4 days, 5 days, 6 days, 7 days, 10 days, 14 days, 21 days, 30 days, or more than 30 days. Moreover, treatment of a subject with a therapeutically effective amount of the antibodies of the invention can include a single treatment or can include a series of treatments. It will also be appreciated that the effective dosage of an antibody used for treatment may increase or decrease over the course of a particular treatment. Changes in dosage may result and become apparent from the results of diagnostic assays or imaging techniques for detecting tumor sizes known in the art. In some embodiments of the invention, the method comprises administration of the antibodies at several time per day, including but not limiting to 2 times per day, 3 times per day, and 4 times per day.

The disclosure includes all amino acid sequences described herein, and all polynucleotides encoding the amino acid sequences. The disclosure also includes all amino acid sequences that have at least 80% similarity to any amino acid sequence described herein. The percent amino acid sequence can be determined across the full length of any amino acid sequence described herein, or across any contiguous amino acid sequence that constitutes a functional antibody, such as an antibody that targets LANCL1, non-limiting examples of which are provided below. As such, the disclosure includes sequences that are the same as any amino acid or nucleotide sequence described herein, and from 80, 81, 82, 83, 84, 85, 86, 87, 88, 89, 90, 91, 92, 93, 94, 95, 96, 97, 98, 99% identical to such sequences.

As used herein, the terms "identical" or percent "identity", in the context of describing two or more polynucleotide or amino acid sequences, refer to two or more sequences or subsequences that are the same or have a specified percentage of amino acid residues or nucleotides that are the same (for example, a mutant protein used in the method of this invention has at least 80% sequence identity, preferably 85%, 90%, 91%, 92%, 93, 94%, 95%, 96%, 97%, 98%, 99%, or 100% identity, to a reference sequence), when compared and aligned for maximum correspondence over a comparison window, or designated region as measured using one of the following sequence comparison algorithms or by manual alignment and visual inspection. Such sequences are then said to be "substantially identical". With regard to polynucleotide sequences, this definition also refers to the complement of a test sequence. The comparison window, in certain embodiments, refers to the full length sequence of a given mRNA sequence or polypeptide.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

LANCL1-Specific Antibodies

The present invention provides antibodies or antigen binding fragments thereof that target Lanthionine synthase C-like protein 1 (LANCL1) protein. In certain embodiments, the antibody is a monoclonal antibody or a polyclonal antibody. In further embodiments, the antibody or antigen binding fragments thereof can be chimeric antibodies, single chain antibodies, scFv antibodies, or Fab fragments. In certain embodiments, variable regions, including variable regions of the heavy and/or light chains, of an antibody that target LANCL1 can be linked to a human antibody constant fragment, including, for example, constant heavy and lights chains of human IgG4 or IgG1.

In certain embodiments, the LANCL1-specific antibody can be conjugated to a label. Non-limiting examples of labels that can be conjugated to the antibodies or antigen binding fragments thereof as disclosed herein include an enzyme, a radioisotope, a fluorescent label, an antibody label, a drug molecule label, or a bioluminescent label. In certain embodiments, the antibody labels can be one or more antibodies or antigen binding fragments that target other antigens or epitopes, including antibodies that are not specific to LANCL1. Examples include, but are not limited, to bispecific antibodies (BsAbs) or multispecific antibodies (MsAbs) which contain two or more binding sites directed at two or more different respective epitopes. In certain embodiments, drug molecule labels can be any cytotoxic drug that kill tumor cells. Examples include, but are not limited to, a DNA damaging agent, microtubule disrupting agent, small molecule inhibitor, protein kinase inhibitor, such as, for example, sorafenib and related compounds, and inhibitors of major oncogenic signaling pathways. Additional embodiments of labels can be conjugated/coupled to the antibodies and antigen binding fragments thereof and various methods of detecting the labels are provided.

In preferred embodiments, the antibody is H00010314-A01 antibody (Abnova, Taipei, Taiwan), HPA034994 antibody (Sigma-Aldrich, St. Louis, MO), or NBP1-81796 antibody (Novus Biologicals, Centennial Colorado).

In preferred embodiments, the compositions and methods according to the subject invention utilize a LANCL1-specific antibody. A LANCL1-specific antibody may be added to compositions at concentrations of 0.01 to 90% by weight (wt %), preferably 0.1 to 50 wt %, and more preferably 0.1 to 20 wt %. In another embodiment, a purified LANCL1-specific antibody may be in combination with an acceptable carrier, in that a LANCL1-specific antibody may be presented at concentrations of 0.001 to 50% (v/v), preferably, 0.01 to 20% (v/v), more preferably, 0.02 to 10% (v/v). In certain embodiments, the LANCL1-specific antibody can be administered to a subject at a dosage of about 1 mg/kg to about 100 mg/kg.

The subject composition can further comprise one or more pharmaceutically acceptable carriers, and/or excipients, and can be formulated into preparations, for example, liquid forms, such as solutions and injections.

The term "pharmaceutically acceptable" as used herein means compatible with the other ingredients of a pharmaceutical composition and not deleterious to the recipient thereof.

Carriers and/or excipients according the subject invention can include any and all solvents, diluents, buffers (such as, e.g., neutral buffered saline, phosphate buffered saline, or optionally Tris-HCl, acetate or phosphate buffers), oil-in-water or water-in-oil emulsions, aqueous compositions with or without inclusion of organic co-solvents suitable for, e.g., IV use, solubilizers (e.g., Polysorbate 65, Polysorbate 80), colloids, dispersion media, vehicles, fillers, chelating agents (e.g., EDTA or glutathione), amino acids (e.g., glycine), proteins, disintegrants, binders, lubricants, wetting agents, emulsifiers, sweeteners, colorants, flavorings, aromatizers, thickeners (e.g. carbomer, gelatin, or sodium alginate), coatings, preservatives (e.g., Thimerosal, benzyl alcohol, polyquaterium), antioxidants (e.g., ascorbic acid, sodium metabisulfite), tonicity controlling agents, absorption delaying agents, adjuvants, bulking agents (e.g., lactose, mannitol) and the like. The use of carriers and/or excipients in the field of drugs and supplements is well known. Except for any conventional media or agent that is incompatible with the target health-promoting substance or with the composition, carrier or excipient use in the subject compositions may be contemplated.

In one embodiment, the compositions of the subject invention can be formulated for administration via injection, for example, as a solution or suspension. The solution or suspension can comprise suitable non-toxic, parenterally-acceptable diluents or solvents, such as mannitol, 1,3-butanediol, water, Ringer's solution, or isotonic sodium chloride solution, or suitable dispersing or wetting and suspending agents, such as sterile, non-irritant, fixed oils, including synthetic mono- or diglycerides, and fatty acids, including oleic acid. One illustrative example of a carrier for intravenous use includes a mixture of 10% USP ethanol, 40% USP propylene glycol or polyethylene glycol 600 and the balance USP Water for Injection (WFI). Other illustrative carriers for intravenous use include 10% USP ethanol and USP WFI; 0.01-0.1% triethanolamine in USP WFI; or 0.01-0.2% dipalmitoyl diphosphatidylcholine in USP WFI; and 1-10% squalene or parenteral vegetable oil-in-water emulsion. Water or saline solutions and aqueous dextrose and glycerol solutions may be preferably employed as carriers, particularly for injectable solutions. Illustrative examples of carriers for subcutaneous or intramuscular use include phosphate buffered saline (PBS) solution, 5% dextrose in WFI and 0.01-0.1% triethanolamine in 5% dextrose or 0.9% sodium chloride in USP WFI, or a 1 to 2 or 1 to 4 mixture of 10% USP ethanol, 40% propylene glycol and the balance an acceptable isotonic solution such as 5% dextrose or 0.9% sodium chloride; or 0.01-0.2% dipalmitoyl diphosphatidylcholine in USP WFI and 1 to 10% squalene or parenteral vegetable oil-in-water emulsions.

Administration of LANCL1-Specific Antibodies

In certain embodiments, a LANCL1-specific antibody can be administered to a subject. Any means of administration that can permit an inhibitor to contact cells in a subject, including, for example, orally, intravenously, intraperitoneally, intramuscularly, intrathecally, or subcutaneously are envisioned in the subject methods. In preferred embodiments, LANCL1-specific antibody can be administered intravenously.

In certain embodiments, a LANCL1-specific antibody can contact healthy cells of subject and/or tumor cells or cancerous cells. In certain embodiments, a LANCL1-specific antibody can contact cells in the liver, including cancerous liver cells. In certain embodiments, a humanized LANCL1-specific antibody can inhibit hepatocellular carcinoma and other solid tumors. The LANCL1-specific antibody can bind to protein on the surface of cells of a subject, including, for example, cancerous cells. In certain embodiments, the LANCL1-specific antibody can inhibit the growth of tumor cells. The LANCL1-specific antibody can inhibit the growth of tumor cells by modulating the LANCL1expression and/or the function of LANCL1. In certain embodiments, the LANCL1-specific antibody can modify the intracellular ROS levels in cells, specifically in HCC cells. For example, cell surface LANCL1 can suppress intracellular ROS levels; therefore, a LANCL1-specific antibody can block such function, leading to an increase in intracellular ROS levels that can be lethal or damaging to the HCC cells.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1—Identification of LANCL1 as a Potential Surface Marker

Since TICs are characterized by specific cell surface markers, we compiled a comprehensive gene list based on the genes of the cluster of differentiation family (defined by HUGO Nomenclature Committee) and the Gene Ontology term "intrinsic component of plasma membrane" (GO: 0031226) (defined by MSigDB v6.0). The list includes all annotated genes related to cellular membranes, including plasma membrane and membranes of intracellular organelles. Based on the rationale that TICs are likely to be present in greater number in the tumors (T) than the corresponding non-tumorous liver (NTL) and our purpose to identify TIC markers specific to tumor for potential therapeutic targeting, we first filtered the above membrane-related gene list with the inclusion criterion that these candidate genes were upregulated in HCC. We derived the differential expression data from both our in-house (41 tumor-non-tumor pairs) and TCGA (50 T-NTL pairs) RNA-sequencing datasets. Gene upregulation was determined by differential expression using a threshold of false discovery rate (FDR) of <0.05. Only genes with substantial expression of log 2(count per million)>1 were included. We were then able to shortlist 134 membrane-related genes consistently upregulated in the tumors than the corresponding NTL.

We then interrogated the 134 shortlisted gene candidates using Dharmacon Cherry-pick ON-Targetplus (Lafayette, CO) custom-made siRNA library for functional screening as outlined in FIG. 1A. Each candidate gene was targeted by a mixture of 4 siRNAs (SMARTpool format) of known siRNA sequences. In this search, we used the sphere forming ability as an initial functional readout. Sphere formation assay is an in vitro test for self-renewal ability characteristic of liver TICs. We have established the platform to perform sphere formation assay on 96-well plates in a high-throughput fashion (4), which is hereby incorporated by reference, as a quick means to screen out targets with functional effects for further validation. In brief, we seeded the siRNA-transfected cells onto the plates and assessed the numbers of spheres formed over 14 days. We have experience that the two human HCC cell lines, PLC/PRF/5 and MHCC97L, form spheres within this time frame while the suppression of the respective gene expression by the siRNAs can be observed and maintained in the first week (4), so that the effects of the respective gene knockdown on sphere formation initiation could be efficiently evaluated with this approach.

Figure 1B:
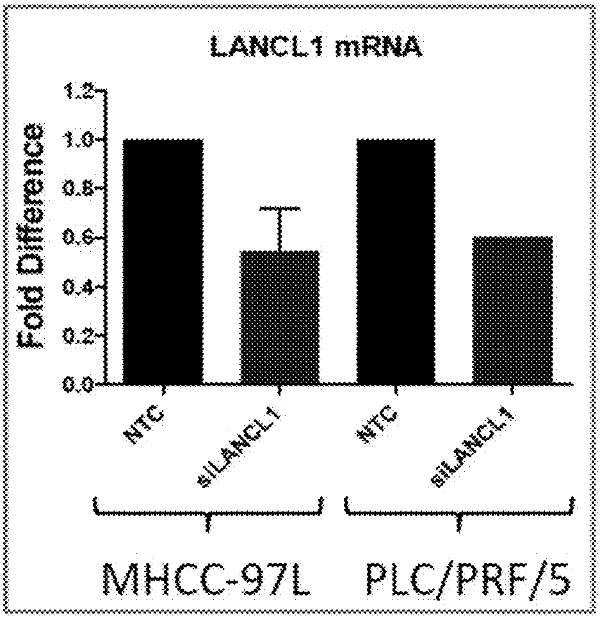
FIGS. 1B-1C Knockdown (KD) efficiency of LANCL1 and the suppression in sphere formation in HCC cell lines in the siRNA functional screening.
Figure 1C:
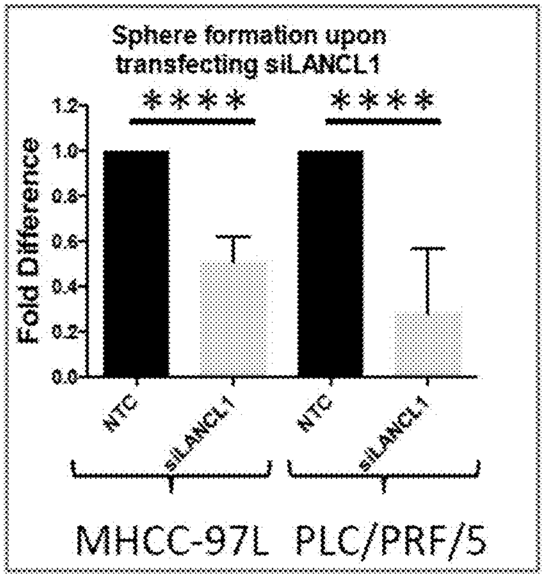
Figure 1D:
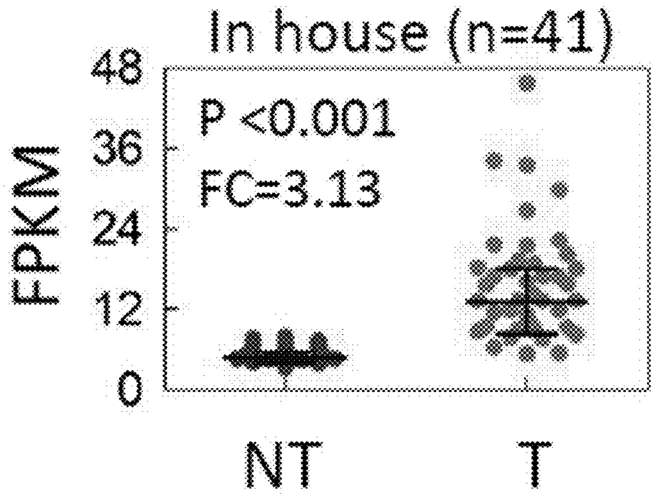
FIGS. 1D-1G LANCL1 mRNA is overexpressed in HCC in TCGA and in-house HCC cohorts.
Figure 1E:
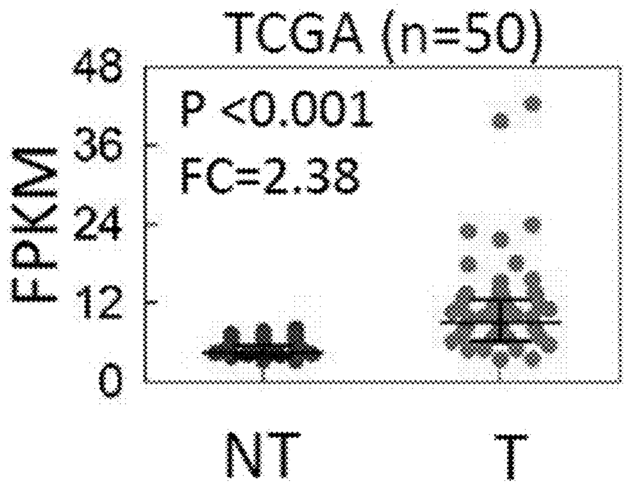
Figure 1F:
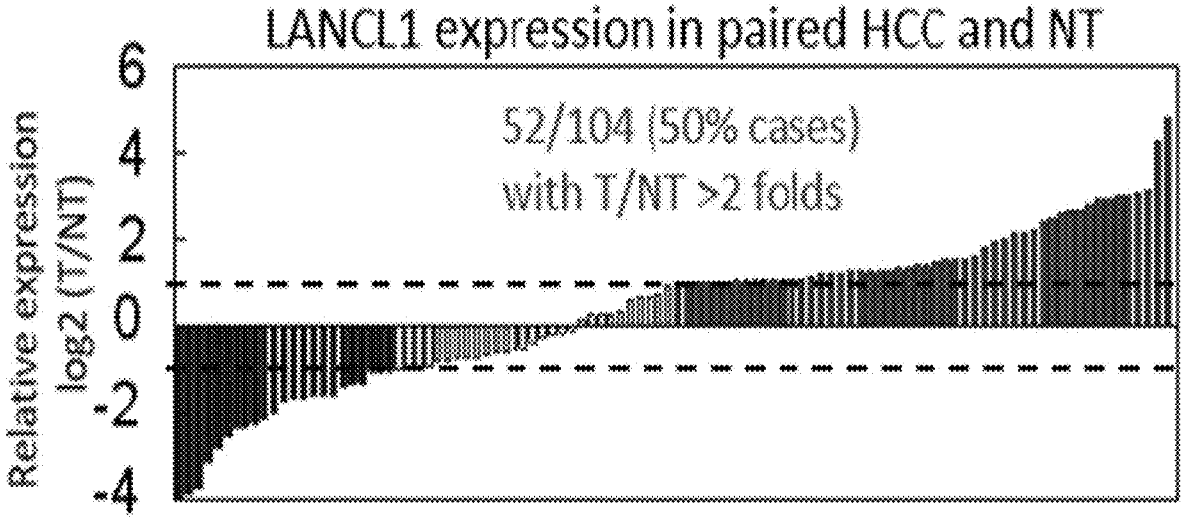
Figure 1G:
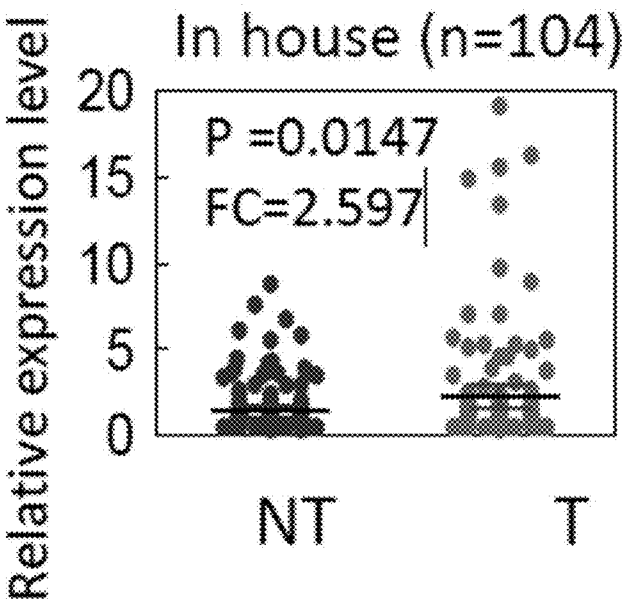

Next, using the criterion that the corresponding siRNA significantly suppressed sphere formation as compared to the non-target control (NTC) by ≥2 folds in at least four of the six trials in both PLC/PRF/5 and MHCC-97L cells (FIG. 1A), we identified 9 gene targets, which were further narrowed down to 6, based on the criterion that these gene targets were not well characterized in HCC stemness in the literature and were potential novel targets. Among these candidates, Lanthionine synthase C-like protein 1 (LANCL1) gene was selected for further characterization because of its promising preliminary data (see below). The knockdown (KD) efficiency by LANCL1 siRNAs was validated by real-time quantitative PCR (qPCR) in both PLC/PRF/5 and MHCC-97L cells (FIG. 1B), with reduction of the respective sphere forming ability (FIG. 1C).

Figure 1H:
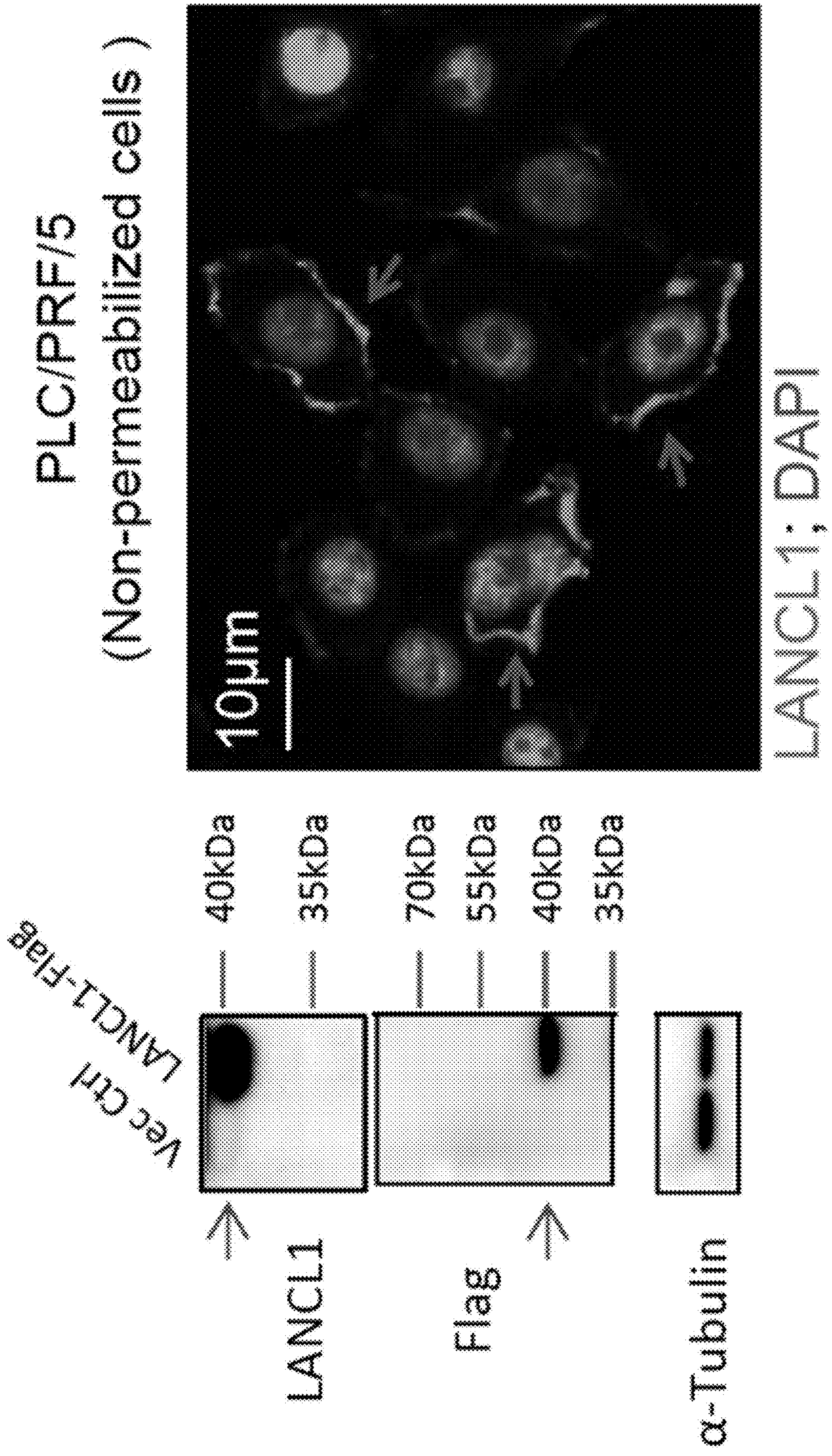
FIG. 1H Cell membrane localization of Flag-tagged LANCL1 protein in PLC/PRF/5 cells.
Figure 1I:
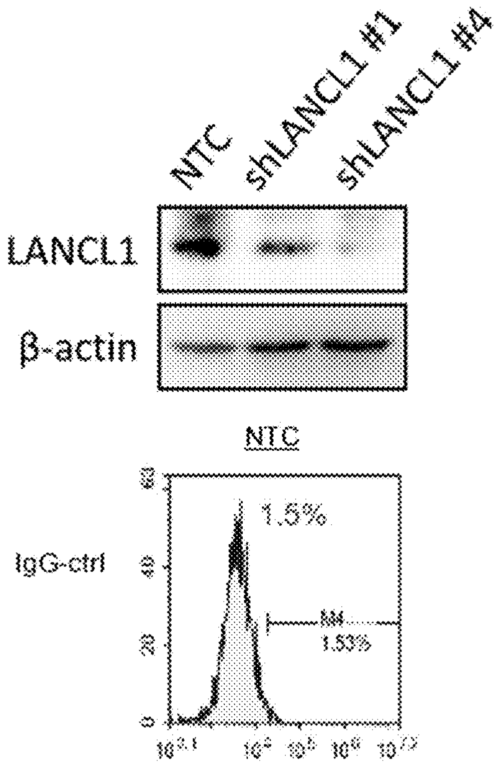
Figure 1J:
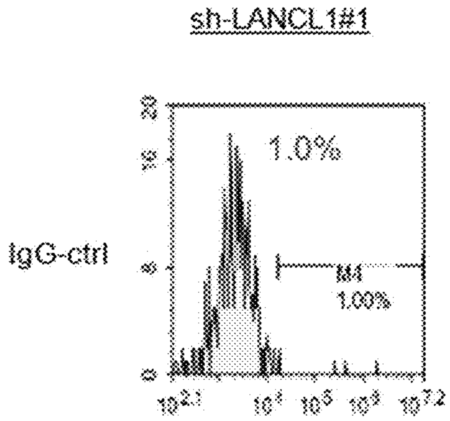
Figure 1K:
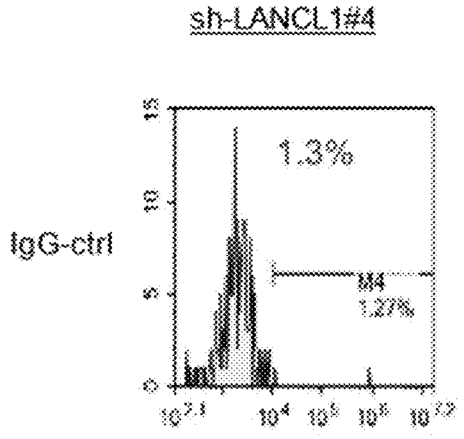
Figure 1L:
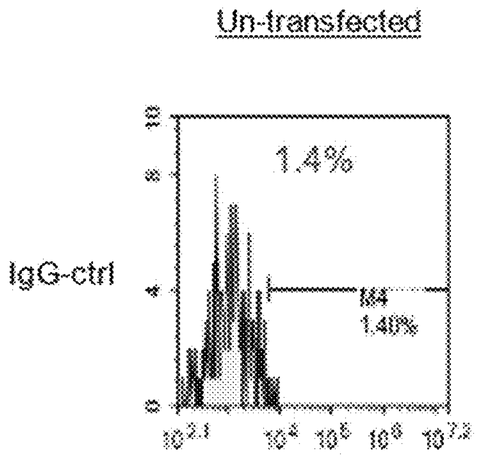
Figure 1M:
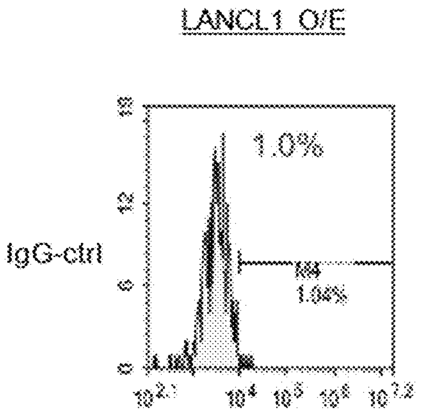
Figure 1N:
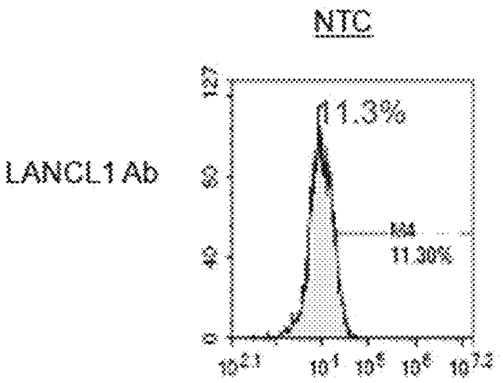
Figure 1O:
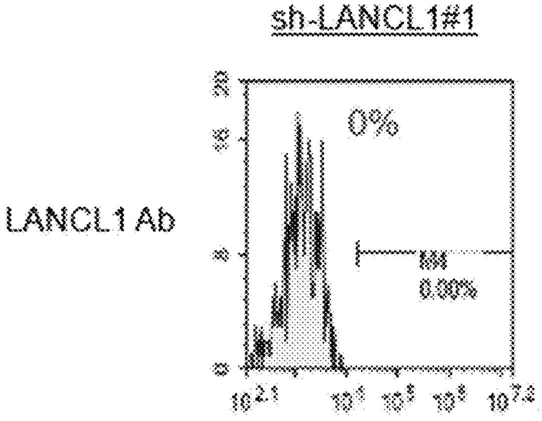
Figure 1P:
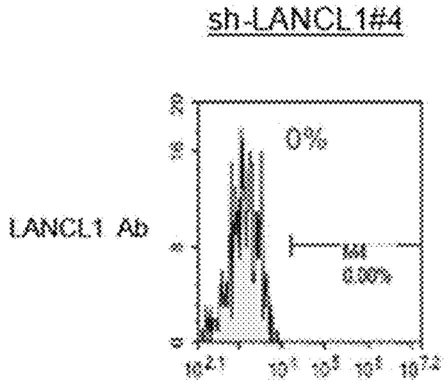
Figure 1Q:
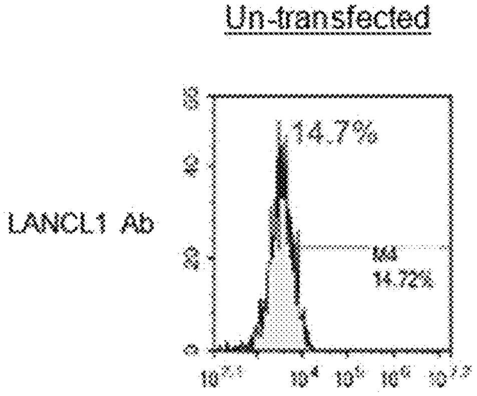
Figure 1R:
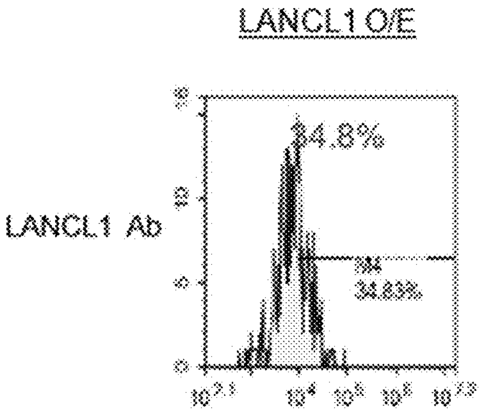

Example 2—LANCL1 is Overexpressed in HCC and its Protein Expression at the Cell Surface is Validated LANCL1 has only been scarcely reported. LANCL1 is a membranous glutathione-S-transferase catalyzing the conjugation of glutathione (GSH) to mitigate neuronal oxidative stress through GSH antioxidant defense mechanism (5). Its functions have been well characterized in neuronal cells but rarely in cancer cells. In prostate cancer, it was reported to promote prostate cancer cell proliferation by protecting cells from damage caused by oxidative stress. Knockdown of LANCL1 resulted in increased cancer cell apoptosis as LANCL1 reduced cell death via suppression of JNK signaling pathway. Clinical data also showed that LANCL1 upregulation in human prostate cancers correlated with tumor progression (6). There is a suggestion that LANCL1 may play an oncogenic role in cancer progression. However, for HCC, there were no studies regarding LANCL1 so far. In particular, it has not been reported as a TIC marker in liver cancer or any other cancers, and its functions in HCC are unknown. Here, we show that LANCL1 is overexpressed in our expanded in-house (104 tumor-non-tumor pairs) and TCGA (50 T-NTL pairs) datasets (FIGS. 1D-1G). Furthermore, with immuno-fluorescent imaging on PLC/PRF/5 cells transfected with Flag-tagged LANCL1 protein, we observed prominent membrane localization of the protein (FIG. 1H). Flow cytometry also validated LANCL1 expression in PLC/PRF/5 cells with respective KD and overexpression of LANCL1 proteins using Sigma-Aldrich antibody (HPA034994) that binds to the N-terminal first 47 amino-acids (aa) region upon cell fixation by 4% paraformaldehyde (FIGS. 1I-1R).

Figure 2A:
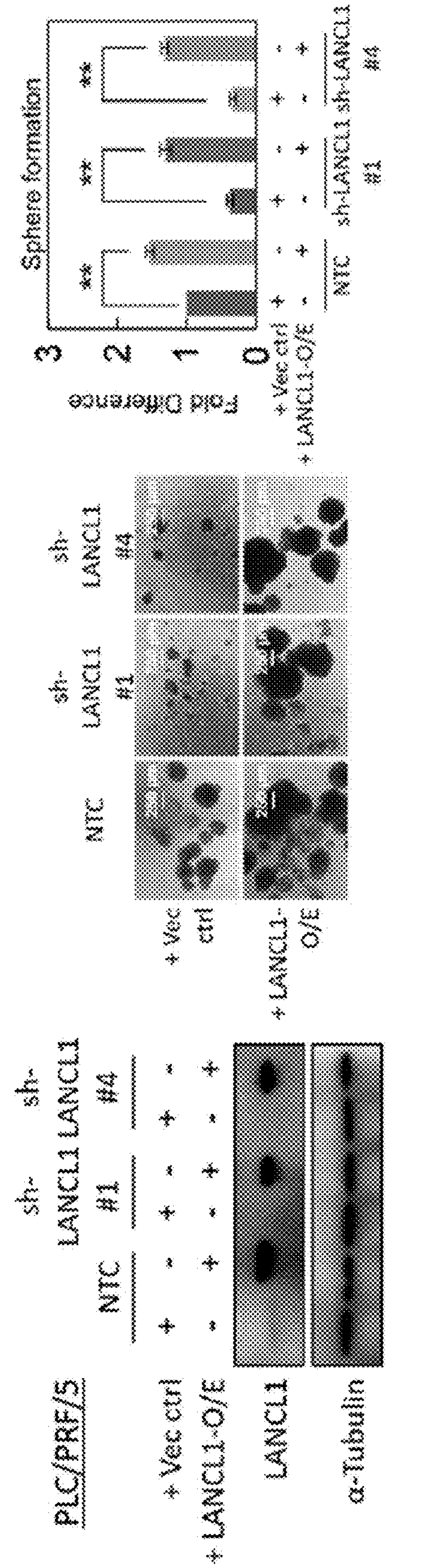
FIGS. 2A-2F LANCL1 promotes sphere formation and tumorigenicity of HCC cells.
Figure 2B:
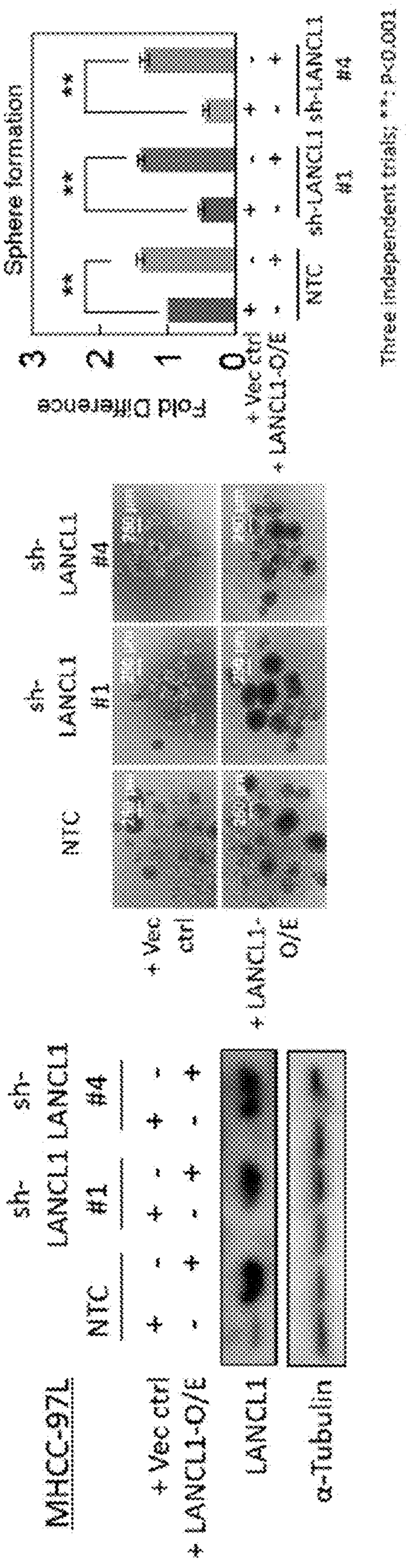

Example 3—Stable LANCL1 Knockdown Abrogated Liver Tic Properties In Vitro in HCC Cell Models and In Vivo in Mouse Models We investigated the liver TIC properties of LANCL1 by (1) creating stable KD using short-hairpin (shRNA) approach and (2) rescue experiment in the LANCL1-KD cells by overexpressing LANCL1 variant not targetable by shRNA but with the same amino acid sequence as the wild-type (WT) LANCL1 protein in PLC/PRF/5 and MHCC97L cells. These helped validate the results of sphere formation assay obtained from the initial screening. The two shRNA sequences (SEQ ID NOs: 1-4) significantly reduced the sphere forming ability, whereas the non-targetable variant LANCL1 overexpression as a rescue enhanced sphere formation and reversed the inhibitory effects of shLANCL1 on sphere formation in both cell lines (FIGS. 2A-2B).

Figure 2C:
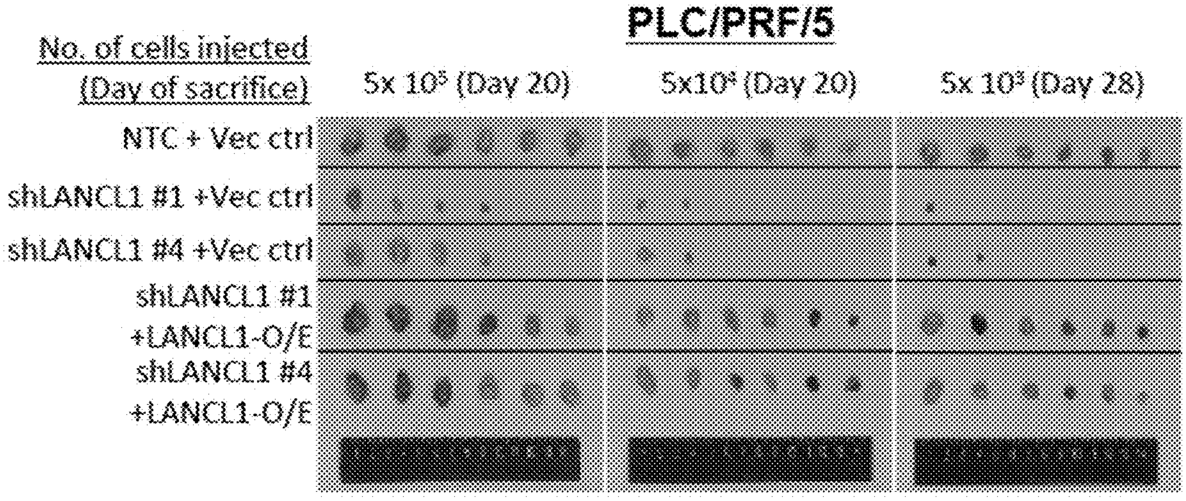
Figure 2D:
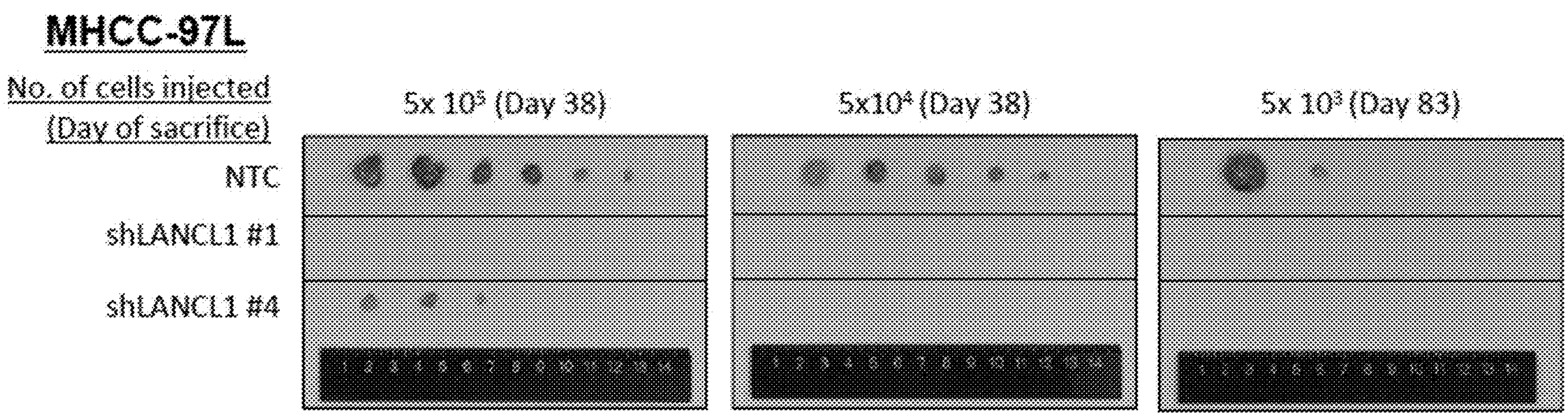

To evaluate the tumor initiation and self-renewal ability of the cells to generate a complete tumor in immunodeficient mice (3), we performed in vivo limiting dilution tumorigenicity assay using subcutaneous xenograft model, as we described previously (7-9). We found that LANCL1 KD significantly suppressed the tumorigenicity of PLC/PRF/5 (FIG. 2C) and MHCC97L cells (FIG. 2D), whereas LANCL1 rescue reversed the inhibitory effects of shLANCL1 on tumorigenicity (FIG. 2C).

Figure 2E:
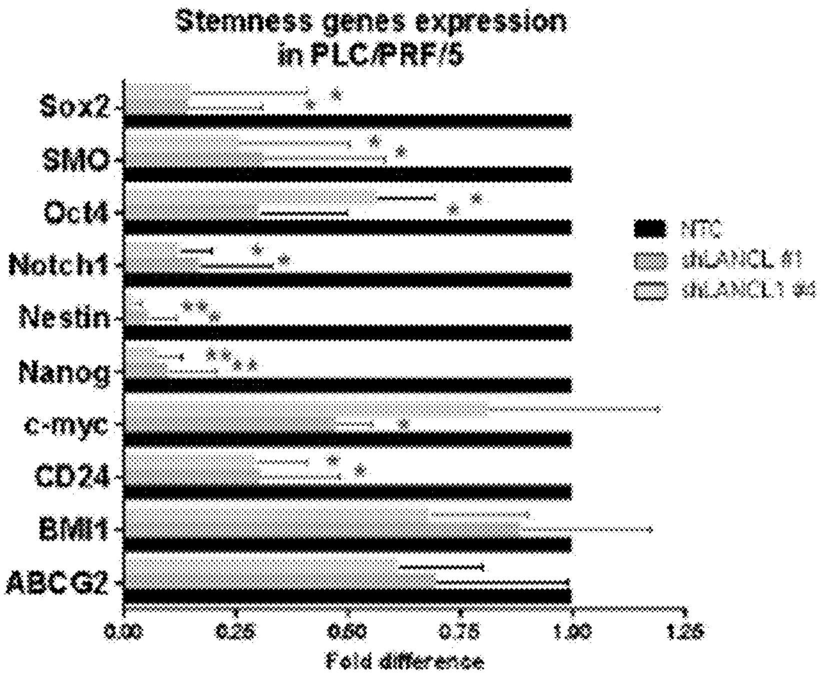
Figure 2F:
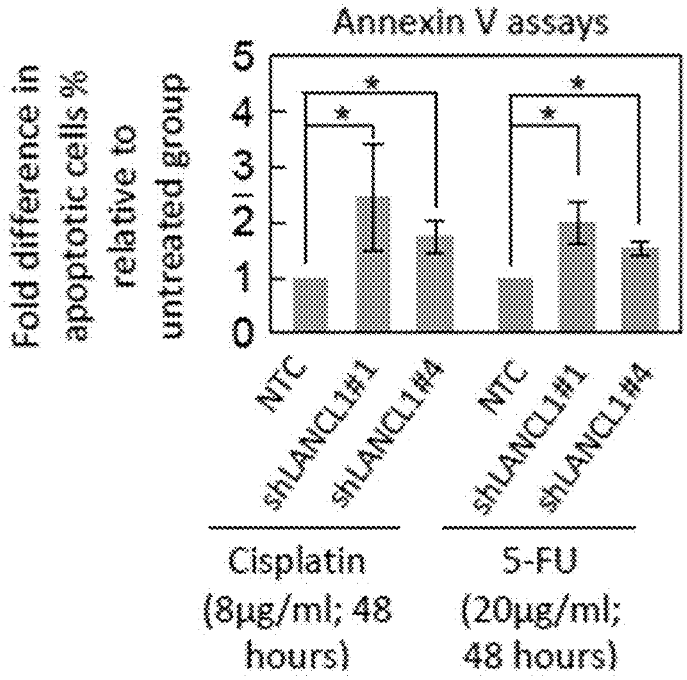

Besides, qPCR analyses showed that LANCL1-KD reduced the expression of various stemness-related genes, including CD24, Nanog, Nestin, Notch1, Oct4, SMO and Sox2 in PLC/PRF/5 (FIG. 2E). As chemoresistance is another key feature of liver TICs, we investigated the effects of LANCL1-KD in sensitizing HCC cells to two chemodrugs, cisplatin and 5-fluoruracil (5-FU). LANCL1-KD significantly sensitized PLC/PRF/5 cells to cisplatin and 5-FU and resulted in increased proportion of apoptotic cells (FIG. 2F).

Figure 3A:
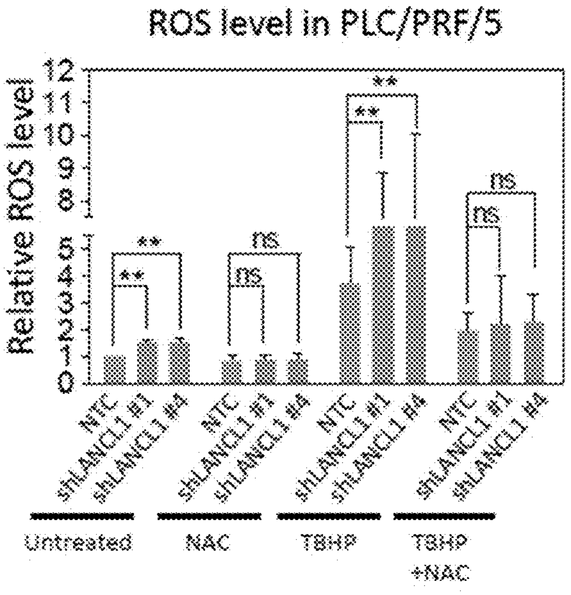
Figure 3B:
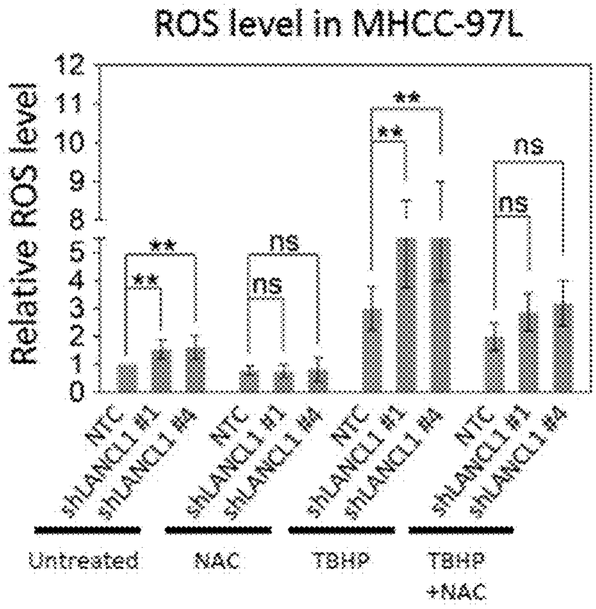
Figure 3C:
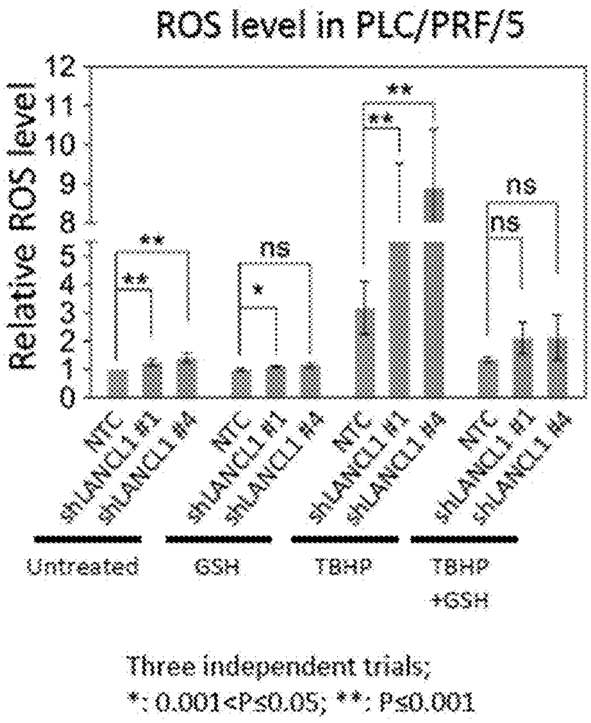
Figure 3D:
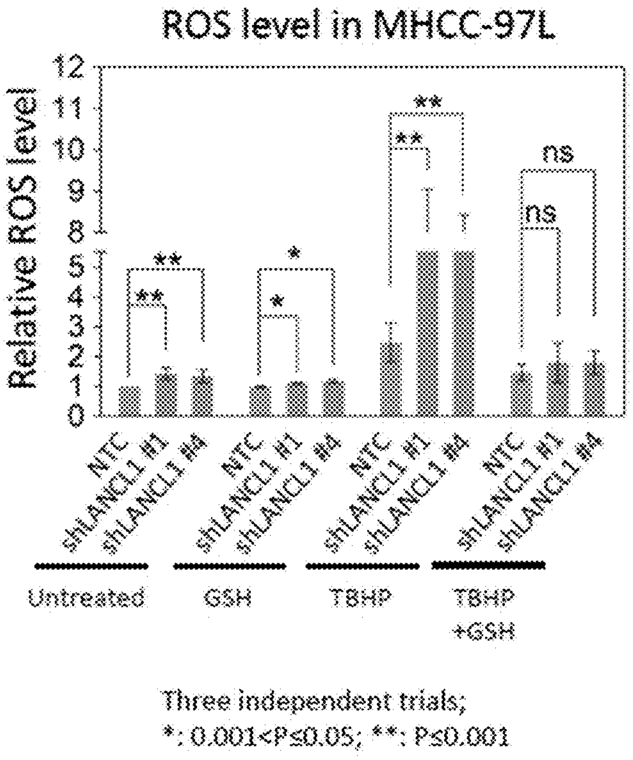
Figure 3E:
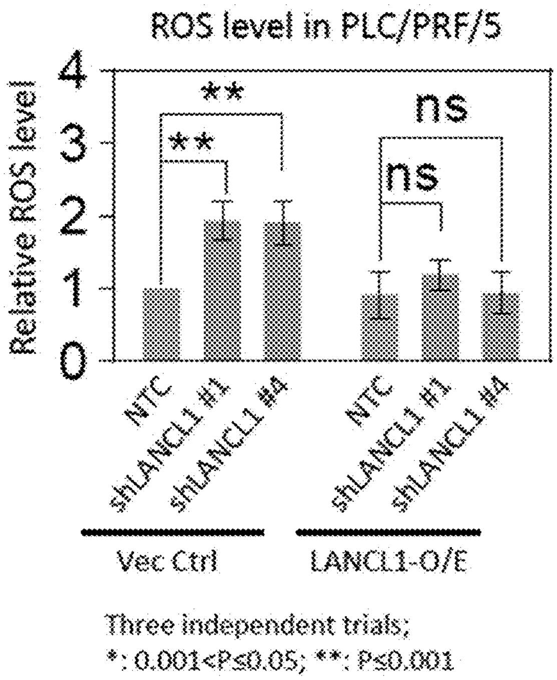
Figure 3F:
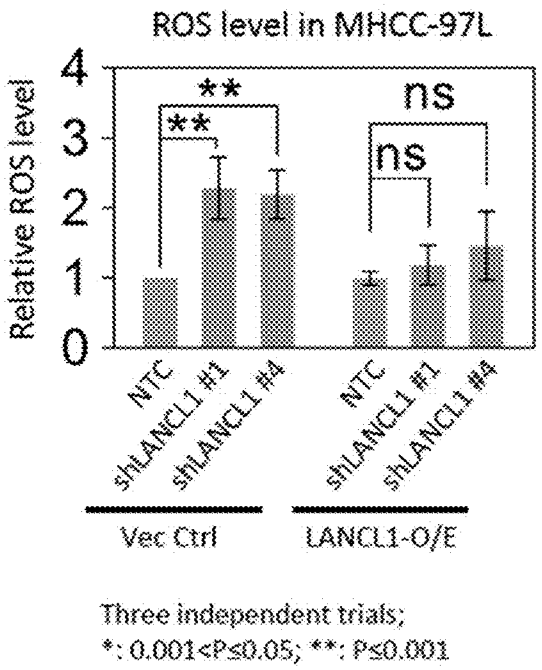
Figure 3G:
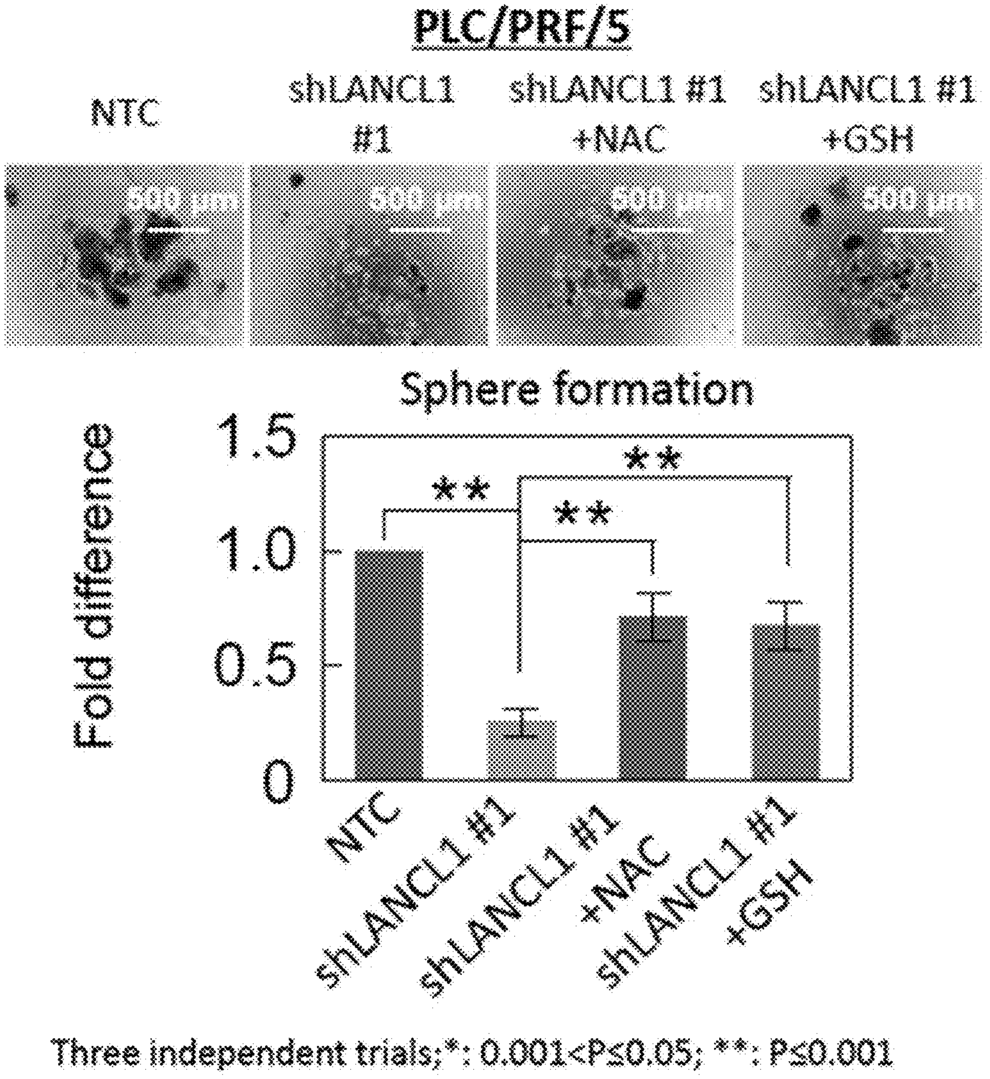
Figure 3H:
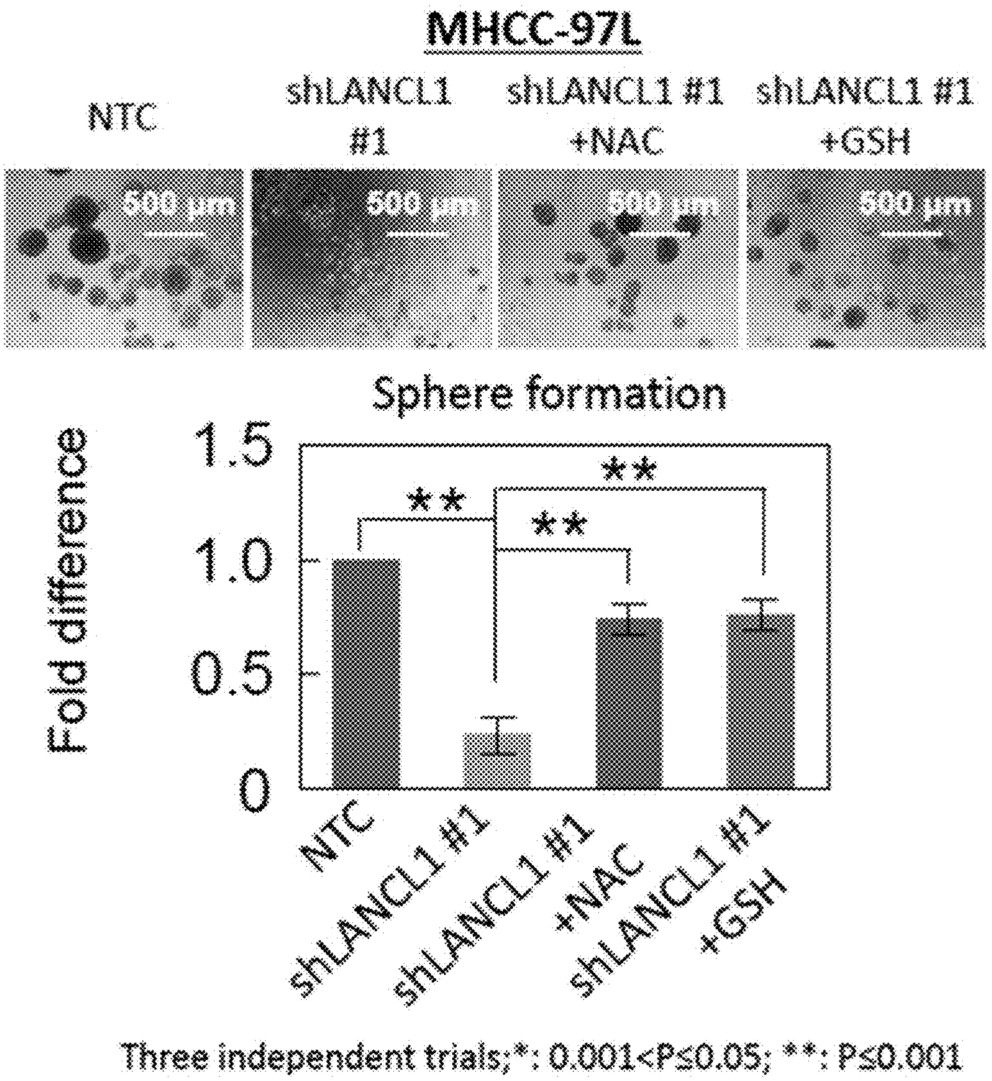
Figure 31:
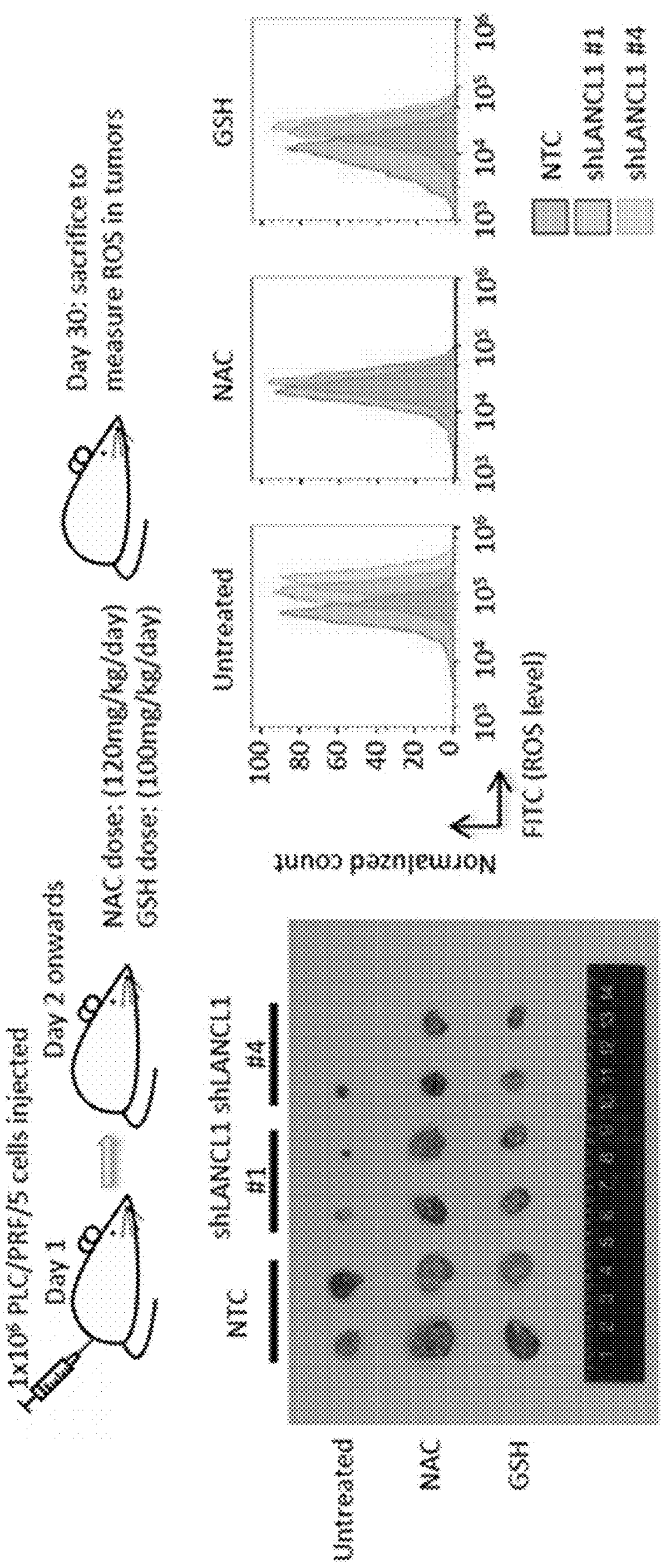

Example 4—LANCL1 Suppresses Reactive Oxygen Species (ROS) Levels in HCC Cells to Promote Liver Tic Properties It has been reported that LANCL1 inhibits JNK pathway to protect prostate cancer cells from oxidative stress (6). LANCL1 also confers anti-oxidant activity to protect against ROS-induced cell damage in neuronal cells (5). We found that LANCL1 reduced the intracellular ROS levels in HCC cells with a set of experiments. LANCL1-KD increased the ROS level in PLC/PRF/5 and MHCC-97L (FIGS. 3A-3F). Such increase in ROS levels was suppressed by addition of the exogenous anti-oxidants N-acetyl cysteine (NAC) and glutathione (GSH). On the contrary, upon addition of the oxidizing agent, tert-Butyl hydroperoxide (TBHP) (FIGS. 3A-3D) to both LANCL1 KD HCC cells, the ROS levels were significantly increased. However, the addition of these antioxidants suppressed the ROS levels enhanced by the oxidizing agent TBHP (FIGS. 3A-3D). More interestingly, the rescue of LANCL1 suppressed the ROS levels raised by LANCL1-KD (FIGS. 3E-3F) in both PLC/PRF/5 and MHCC-97L, indicating the suppressive role of LANCL1 in intracellular ROS level. Then, we found that when we administered exogenous anti-oxidants NAC and GSH to the LANCL-KD cells, the sphere formation originally suppressed by LANCL1-KD could be rescued in both HCC cell lines (FIGS. 3G-3H). Further investigation into the xenograft tumor tissues of LANCL1-KD cells revealed increased ROS levels in vivo upon LANCL1-KD as compared to NTC (FIG. 3I) but that was abolished when anti-oxidants NAC or GSH were administered. These findings suggest that LANCL1 reduces the intracellular ROS levels in HCC cells to promote liver TIC properties and tumorigenicity.

Figure 4A:
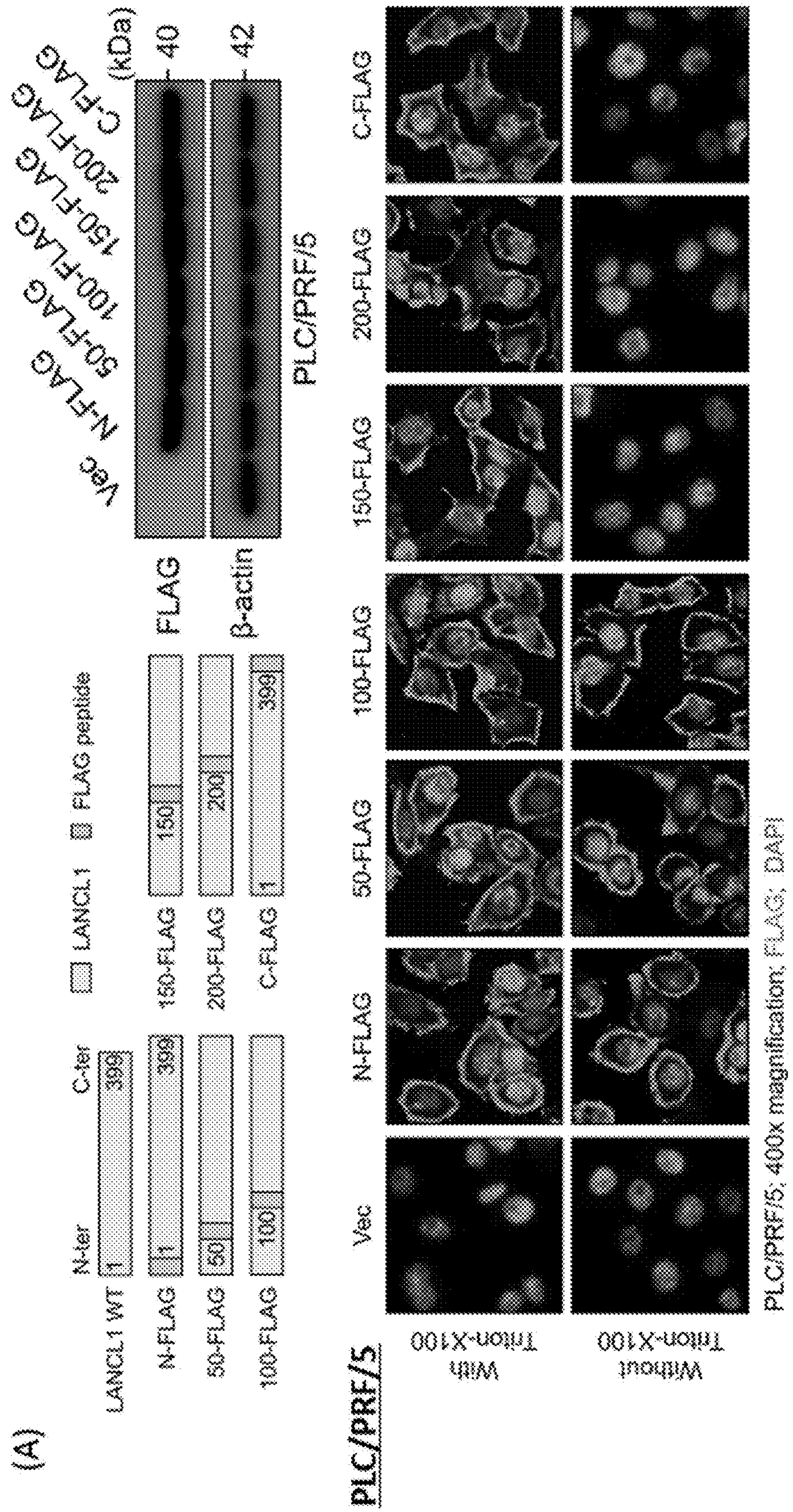
FIGS. 4A-4B Characterization of the structure and orientation of LANCL1 protein on cell membrane of HCC cells.
Figure 4B:
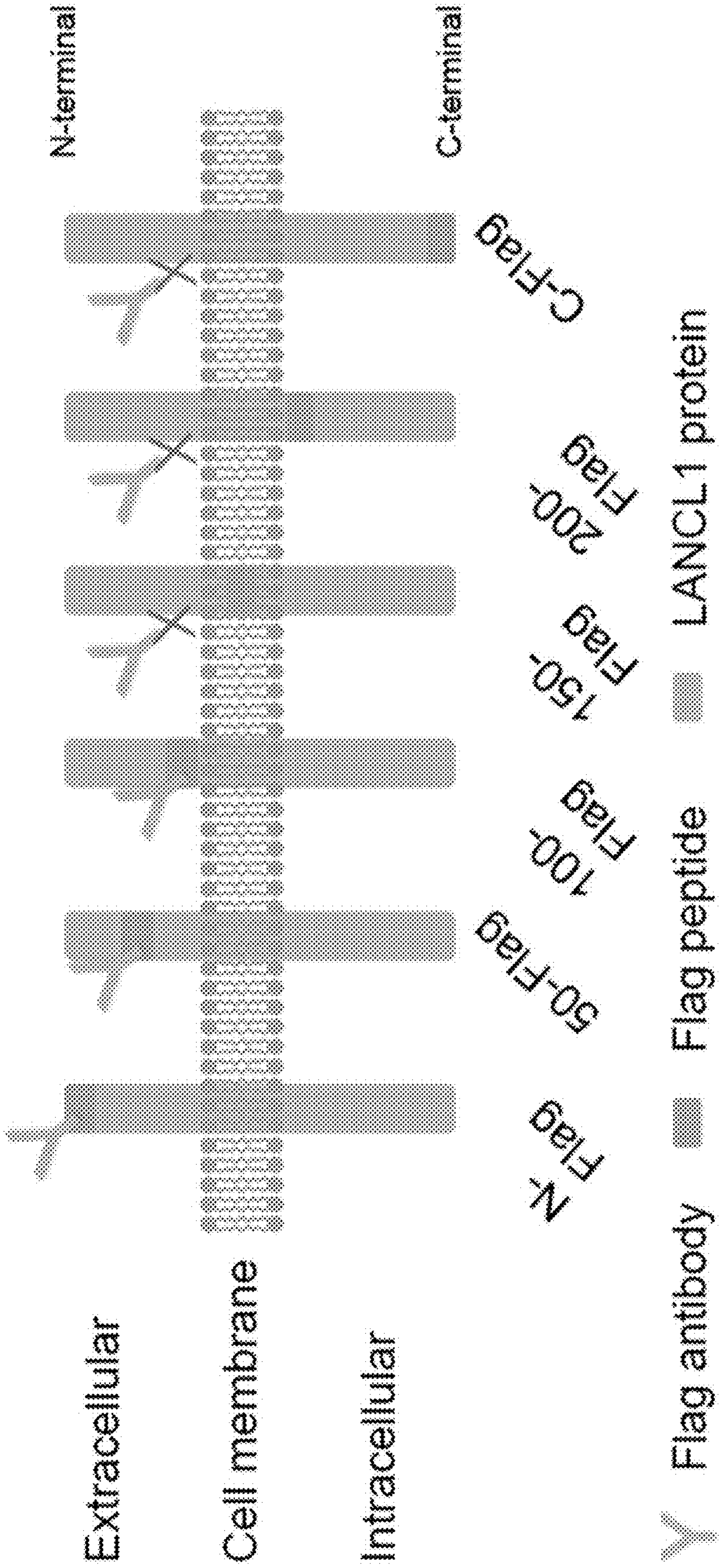

Example 5—Characterization of the Structure and Orientation of LANCL1 Protein on Cell Membrane of HCC Cells Since the protein structure and orientation of LANCL1 protein on cell membrane were not well-reported, we cloned the various mutants of LANCL1 with insertion of Flag tag at different positions in the protein (FIG. 4A) and then made use of immunofluorescence with anti-Flag antibodies to examine the PLC/PRF/5 cells transfected with the various mutants in the presence and absence of cell membrane permeabilization with triton X-100 (FIG. 4B).

The N-terminal Flag-tag was detectable irrespective of membrane permeabilization, indicating the extracellular localization of the N-terminal of LANCL1 protein (FIG. 4A). Similar phenomenon was observed for LANCL1 mutants with Flag-tag inserted at the 50th and 100th aa-positions (FIG. 4A). On the contrary, the C-terminal Flag-tag and those Flag-tags inserted at the 150th and 200th aa-positions were only detected upon membrane permeabilization, indicating (1) the intracellular localization of the C-terminal of LANCL1 protein and (2) the transmembrane region localized between the 100th and 150th aa-positions of the protein (FIG. 4A).

Figure 5:
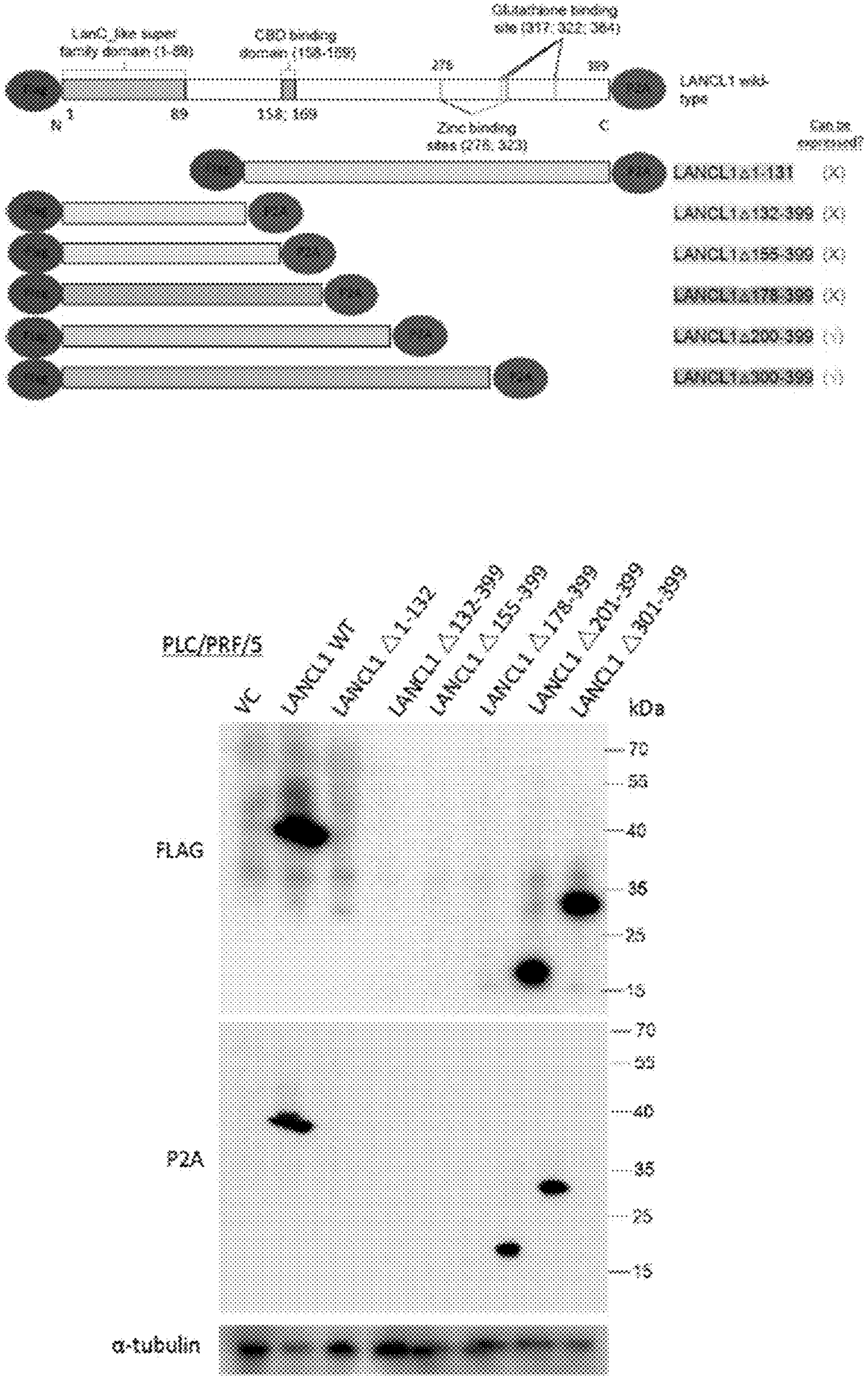
FIG. 5 Characterization of the truncation mutants of LANCL1 protein in HCC cells. Truncated LANCL1 mutants revealed the importance of the first N-terminal 200 amino acids for LANCL1 protein expression.

Example 6—Characterization of the Truncation Mutants of LANCL1 Protein in HCC Cells We cloned various C-terminal truncated mutants of LANCL1 and found that the protein could be expressed only when the truncation was less than 200aa from the C-terminus (FIG. 5). We also cloned the N-terminal truncated mutant and found the protein could not be expressed even when the first 131aa was truncated. This indicates that an intact portion of the first 200aa from the N-terminus (i.e. the extracellular N-terminal region) is important for LANCL1 protein expression (FIG. 5). This information will be important for the targeting of the LANCL1 proteins for translational application in future (see Example 7).

Example 7—Testing Antibodies Specifically Against the N-Terminal of the LANCL1 Proteins in Sphere Formation of HCC Cells for Exploring the Translational Application of the Antibodies in Management and Treatment of HCC To this end, our invention is to employ anti-LANCL1 antibodies or LANCL1 inhibition to eliminate liver TICs for treatment of HCC. To allow the druggability of liver TICs without artificially permeabilizing the cells, we need to use antibodies that specifically target the extracellular N-terminal region of LANCL1 protein. There are anti-LANCL1 antibodies available in the market, including HPA034994 by Sigma-Aldrich, ab151290 by Abcam (Cambridge, United Kingdom), H00010314-A01 by Abnova (Taipei City, Taipei, Taiwan), 32098-05141 by AssayPro (St. Charles, MO) and NBP1-81796 by Novus Biologicals (Hong Kong, China) (FIG. 6A). However, some of them are not suitable for translational purpose. For example, the one by Abcam (ab151290) targets the 104-399 aa region, which is not sufficient to cover the extracellular N-terminal region of LANCL1. On the other hand, the AssayPro antibody (32098-05141) is conjugated with fluorophore FITC and is not suitable for translational use. This leaves only the polyclonal antibodies by Novus Biologicals (NBP1-81796), Sigma-Aldrich (HPA034994) and Abnova (H00010314-A01) respectively, for further functional testing and exploration for future translational purpose. It is also of note that these antibodies target the N-terminal region of LANCL1 protein and some of them show membranous positive staining in the IHC images provided by the respective companies.

Figure 6B:
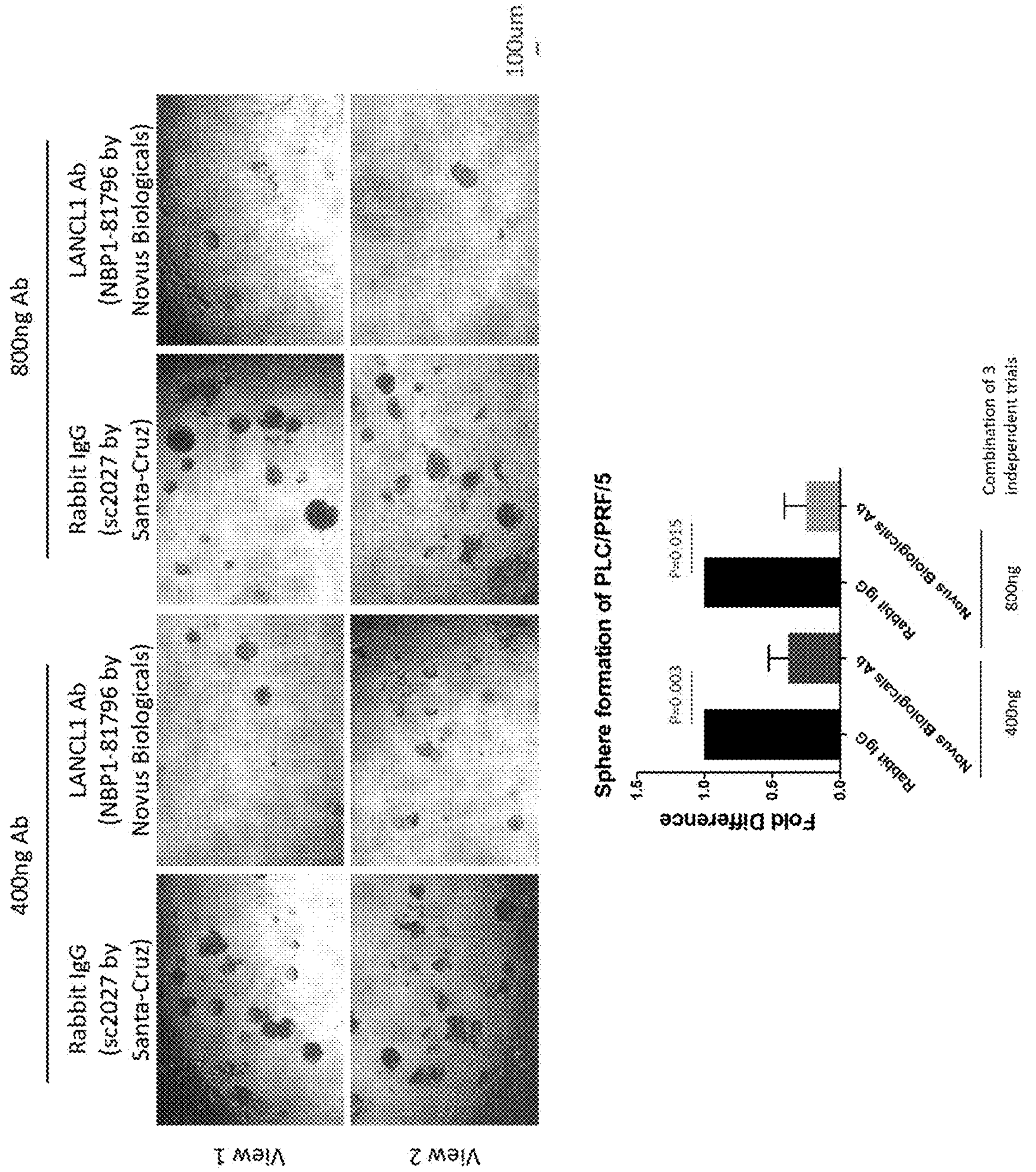
Figure 6C:
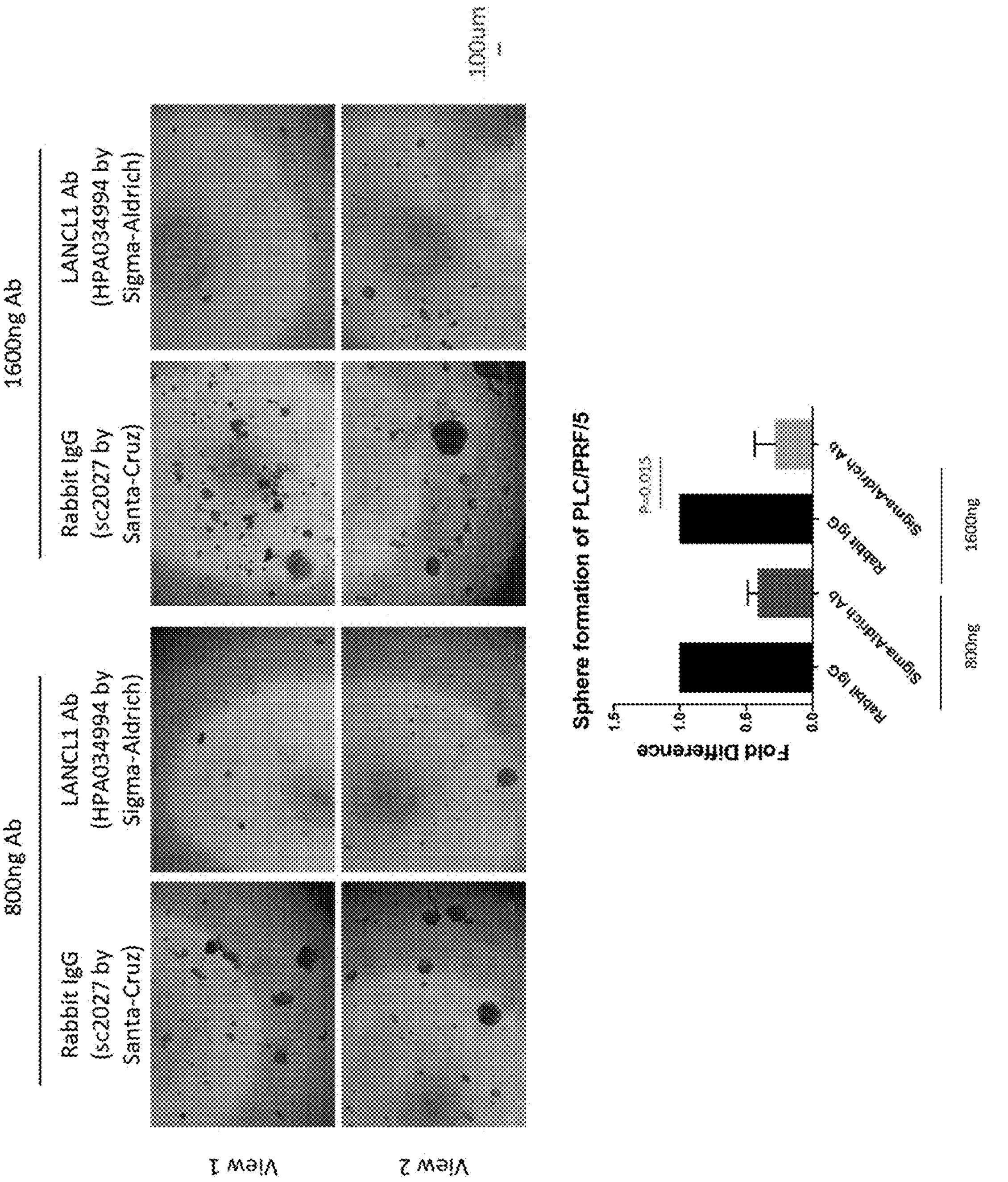
Figure 6D:
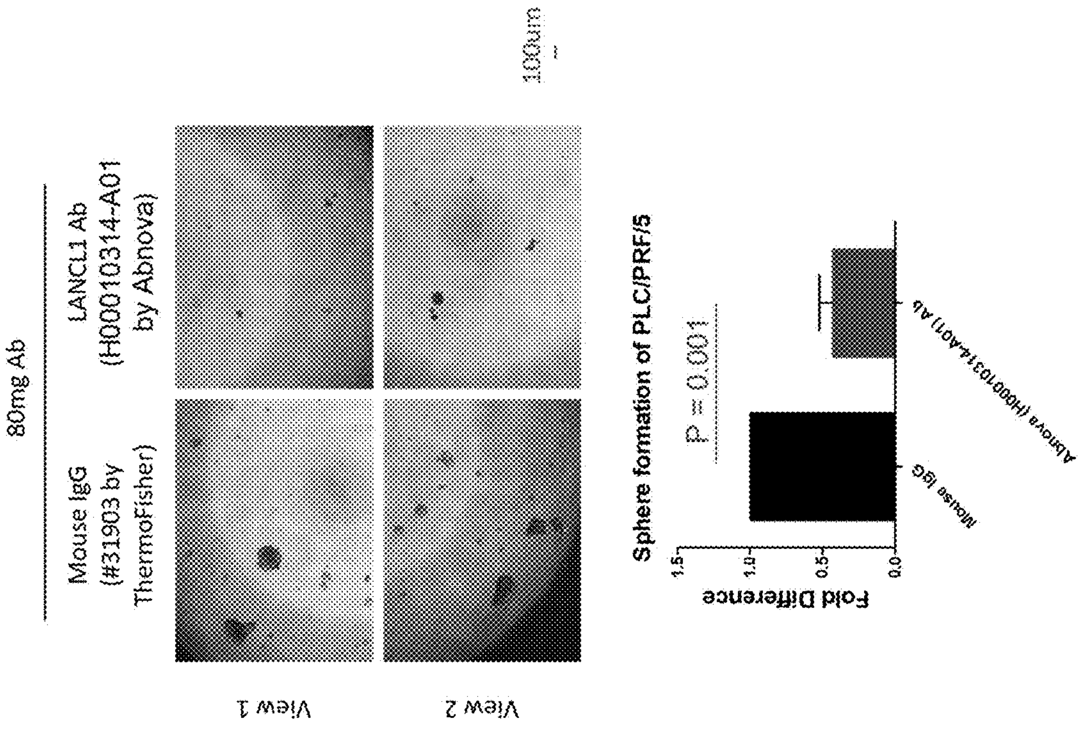

To test the effects of the antibodies on liver TIC properties, we used sphere formation as a functional readout, as it is one of the golden standards for evaluating liver TIC property in vitro in a convenient manner. We used the corresponding mouse or rabbit IgG as reference controls for comparison. We found that the antibodies by Novus Biologicals (NBP1-81796), Sigma-Aldrich (HPA034994) and Abnova (H00010314-A01) significantly suppressed sphere formation of PLC/PRF/5 cells (FIG. 6B, FIG. 6C and FIG. 6D). This implicates the potential use of these antibodies to target LANCL1 protein extracellular region for future translational application.

SEQUENCES

SEQ ID NO: 1: oligo (forward) sequence 1 for cloning the shRNA targeting LANCL1:
CCGGTCACAACGCTTGACCAATACTCGAGTATTGGTCAAGCGTTGTGATTTTTG SEQ ID NO: 2: oligo (reverse) sequence 2 for cloning the shRNA targeting LANCL1:
AATTCAAAAATCACAACGCTTGACCAATACTCGAGTATTGGTCAAGCGTTGTGA SEQ ID NO: 3: oligo (forward) sequence 3 for cloning the shRNA targeting LANCL1:
CCGGGATGTGATCTGGCAATATGCTCGAGCATATTGCCAGATCACATCTTTTTG SEQ ID NO: 4: oligo (reverse) sequence 4 for cloning the shRNA targeting LANCL1:
AATTCAAAAAGATGTGATCTGGCAATATGCTCGAGCATATTGCCAGATCACATC SEQ ID NO: 5: LANCL1 amino acid sequence:
MAQRAFPNPYADYNKSLAEGYFDAAGRLTPEFSQRLTNKIRELLQQMERGLKSADPRDGTGYTGWAGIAVLYLHLYDVFGDPA
YLQLAHGYVKQSLNCLTKRSITFLCGDAGPLAVAAVLYHKMNNEKQAEDCITRLIHLNKIDPHAPNEMLYGRIGYIYALLFVN
KNFGVEKIPQSHIQQICETILTSGENLARKRNFTAKSPLMYEWYQEYYVGAAHGLAGIYYYLMQPSLQVSQGKLHSLVKPSVD
YVCQLKFPSGNYPPCIGDNRDLLVHWCHGAPGVIYMLIQAYKVFREEKYLCDAYQCADVIWQYGLLKKGYGLCHGSAGNAYAF
LTLYNLTQDMKYLYRACKFAEWCLEYGEHGCRTPDTPFSLFEGMAGTIYFLADLLVPTKARFPAFEL*

SEQ ID NO: 6: nucleotide sequence encoding LANCL1
ATGGCTCAAAGGGCCTTCCCGAATCCTTATGCTGATTATAACAAATCCCTGGCCGAAGGCTACTTTGATGCTGCCGGGAGGCT
GACTCCTGAGTTCTCACAACGCTTGACCAATAAGATTCGGGAGCTTCTTCAGCAAATGGAGAGAGGCCTGAAATCAGCAGACC
CTCGGGATGGCACCGGTTACACTGGCTGGGCAGGTATTGCTGTGCTTTACTTACATCTTTATGATGTATTTGGGGACCCTGCC
TACCTACAGTTAGCACATGGCTATGTAAAGCAAAGTCTGAACTGCTTAACCAAGCGCTCCATCACCTTCCTTTGTGGGGATGC
AGGCCCCCTGGCAGTGGCCGCTGTGCTATATCACAAGATGAACAATGAGAAGCAGGCAGAAGATTGCATCACACGGCTAATTC
ACCTAAATAAGATTGATCCTCATGCTCCAAATGAAATGCTCTATGGGCGAATAGGCTACATCTATGCTCTTCTTTTTGTCAAT
AAGAACTTTGGAGTGGAAAAGATTCCTCAAAGCCATATTCAGCAGATTTGTGAAACAATTTTAACCTCTGGAGAAAACCTAGC
TAGGAAGAGAAACTTCACGGCAAAGTCTCCACTGATGTATGAATGGTACCAGGAATATTATGTAGGGGCTGCTCATGGCCTGG
CTGGAATTTATTACTACCTGATGCAGCCCAGCCTTCAAGTGAGCCAAGGGAAGTTACATAGTTTGGTCAAGCCCAGTGTAGAC
TACGTCTGCCAGCTGAAATTCCCTTCTGGCAATTACCCTCCATGTATAGGTGATAATCGAGATCTGCTTGTCCATTGGTGCCA
TGGCGCCCCTGGGGTAATCTACATGCTCATCCAGGCCTATAAGGTATTCAGAGAGGAAAAGTATCTCTGTGATGCCTATCAGT
GTGCTGATGTGATCTGGCAATATGGGTTGCTGAAGAAGGGATATGGGCTGTGCCACGGTTCTGCAGGGAATGCCTATGCCTTC -continued

SEQUENCES

CTGACACTCTACAACCTCACACAGGACATGAAGTACCTGTATAGGGCCTGTAAGTTTGCTGAATGGTGCTTAGAGTATGGAGA
ACATGGATGCAGAACACCAGACACCCCTTTCTCTCTCTTTGAAGGAATGGCTGGAACAATATATTTCCTGGCTGACCTGCTAG
TCCCCACAAAAGCCAGGTTCCCTGCATTTGAACTCTGA

SEQ ID NO: 7: nucleotide sequence encoding non-shRNA targetable mutant of LANCL1:
ATGGCTCAAAGGGCCTTCCCGAATCCTTATGCTGATTATAACAAATCCCTGGCCGAAGGCTACTTTGATGCTGCCGGGAGGCT
GACTCCTGAGTTCAGCCAGAGACTAACAAACAAGATTCGGGAGCTTCTTCAGCAAATGGAGAGAGGCCTGAAATCAGCAGACC
CTCGGGATGGCACCGGTTACACTGGCTGGGCAGGTATTGCTGTGCTTTACTTACATCTTTATGATGTATTTGGGGACCCTGCC
TACCTACAGTTAGCACATGGCTATGTAAAGCAAAGTCTGAACTGCTTAACCAAGCGCTCCATCACCTTCCTTTGTGGGGATGC
AGGCCCCCTGGCAGTGGCCGCTGTGCTATATCACAAGATGAACAATGAGAAGCAGGCAGAAGATTGCATCACACGGCTAATTC
ACCTAAATAAGATTGATCCTCATGCTCCAAATGAAATGCTCTATGGGCGAATAGGCTACATCTATGCTCTTCTTTTTGTCAAT
AAGAACTTTGGAGTGGAAAAGATTCCTCAAAGCCATATTCAGCAGATTTGTGAAACAATTTTAACCTCTGGAGAAAACCTAGC
TAGGAAGAGAAACTTCACGGCAAAGTCTCCACTGATGTATGAATGGTACCAGGAATATTATGTAGGGGCTGCTCATGGCCTGG
CTGGAATTTATTACTACCTGATGCAGCCCAGCCTTCAAGTGAGCCAAGGGAAGTTACATAGTTTGGTCAAGCCCAGTGTAGAC
TACGTCTGCCAGCTGAAATTCCCTTCTGGCAATTACCCTCCATGTATAGGTGATAATCGAGATCTGCTTGTCCATTGGTGCCA
TGGCGCCCCTGGGGTAATCTACATGCTCATCCAGGCCTATAAGGTATTCAGAGAGGAAAAGTATCTCTGTGATGCCTATCAGT
GTGCTGACGTAATTTGGCAGTACGGGTTGCTGAAGAAGGGATATGGGCTGTGCCACGGTTCTGCAGGGAATGCCTATGCCTTC
CTGACACTCTACAACCTCACACAGGACATGAAGTACCTGTATAGGGCCTGTAAGTTTGCTGAATGGTGCTTAGAGTATGGAGA
ACATGGATGCAGAACACCAGACACCCCTTTCTCTCTCTTTGAAGGAATGGCTGGAACAATATATTTCCTGGCTGACCTGCTAG
TCCCCACAAAAGCCAGGTTCCCTGCATTTGAACTCTGA SEQ ID NO: 8: amino acid sequence of the recombinant C-terminal His-tagged LANCL1 protein for raising antibodies:
MAQRAFPNPYADYNKSLAEGYFDAAGRLTPEFSQRLTNKIRELLQQMERGLKSADPRDGTGYTGWAGIAVLYLHLYDVFGDPA
YLQLAHGYVKQSLNCLTKRSITFLCGDAGPLAVAAVLYHKMNNEKQAEDCITRLIHLNKIDPHAPNEMLYGRIGYIYALLFVN
KNFGVEKIPQSHIQQICETILTSGENLARKRNFTAKSPLMYEWYQEYYVGAAHGLAGIYYYLMQPSLQVSQGKLHSLVKPSVD
YVCQLKFPSGNYPPCIGDNRDLLVHWCHGAPGVIYMLIQAYKVFREEKYLCDAYQCADVIWQYGLLKKGYGLCHGSAGNAYAF
LTLYNLTQDMKYLYRACKFAEWCLEYGEHGCRTPDTPFSLFEGMAGTIYFLADLLVPTKARFPAFELHHHHHH*

SEQ ID NO: 9: nucleotide sequence encoding the recombinant C-terminal His-tagged LANCL1 protein for raising antibodies:
ATGGCTCAAAGGGCCTTCCCGAATCCTTATGCTGATTATAACAAATCCCTGGCCGAAGGCTACTTTGATGCTGCCGGGAGGCT
GACTCCTGAGTTCAGCCAGAGACTAACAAACAAGATTCGGGAGCTTCTTCAGCAAATGGAGAGAGGCCTGAAATCAGCAGACC
CTCGGGATGGCACGGGTTACACTGGCTGGGCAGGTATTGCTGTGCTTTACTTACATCTTTATGATGTATTTGGGGACCCTGCC
TACCTACAGTTAGCACATGGCTATGTAAAGCAAAGTCTGAACTGCTTAACCAAGCGCTCCATCACCTTCCTTTGTGGGGATGC
AGGCCCCCTGGCAGTGGCCGCTGTGCTATATCACAAGATGAACAATGAGAAGCAGGCAGAAGATTGCATCACACGGCTAATTC
ACCTAAATAAGATTGATCCTCATGCTCCAAATGAAATGCTCTATGGGCGAATAGGCTACATCTATGCTCTTCTTTTTGTCAAT
AAGAACTTTGGAGTGGAAAAGATTCCTCAAAGCCATATTCAGCAGATTTGTGAAACAATTTTAACCTCTGGAGAAAACCTAGC
TAGGAAGAGAAACTTCACGGCAAAGTCTCCACTGATGTATGAATGGTACCAGGAATATTATGTAGGGGCTGCTCATGGCCTGG
CTGGAATTTATTACTACCTGATGCAGCCCAGCCTTCAAGTGAGCCAAGGGAAGTTACATAGTTTGGTCAAGCCCAGTGTAGAC
TACGTCTGCCAGCTGAAATTCCCTTCTGGCAATTACCCTCCATGTATAGGTGATAATCGAGATCTGCTTGTCCATTGGTGCCA
TGGCGCCCCTGGGGTAATCTACATGCTCATCCAGGCCTATAAGGTATTCAGAGAGGAAAAGTATCTCTGTGATGCCTATCAGT
GTGCTGACGTAATTTGGCAGTACGGGTTGCTGAAGAAGGGATATGGGCTGTGCCACGGTTCTGCAGGGAATGCCTATGCCTTC
CTGACACTCTACAACCTCACACAGGACATGAAGTACCTGTATAGGGCCTGTAAGTTTGCTGAATGGTGCTTAGAGTATGGAGA
ACATGGATGCAGAACACCAGACACCCCTTTCTCTCTCTTTGAAGGAATGGCTGGAACAATATATTTCCTGGCTGACCTGCTAG
TCCCCACAAAAGCCAGGTTCCCTGCATTTGAACTCCATCATCACCATCACCACTGA SEQ ID NO: 10: amino acid sequence of the recombinant N-terminal GST-tagged LANCL1 protein 1-42amino acid region for raising antibodies:
MSPILGYWKIKGLVQPTRLLLEYLEEKYEEHLYERDEGDKWRNKKFELGLEFPNLPYYIDGDVKLTQSMAIIRYIADKHNMLG
GCPKERAEISMLEGAVLDIRYGVSRIAYSKDFETLKVDFLSKLPEMLKMFEDRLCHKTYLNGDHVTHPDFMLYDALDVVLYMD
PMCLDAFPKLVCFKKRIEAIPQIDKYLKSSKYIAWPLQGWQATFGGGDHPPKSDLVPRGSMAQRAFPNPYADYNKSLAEGYFD
AAGRLTPEFSQRLTNKIRE*

SEQ ID NO: 11: nucleotide sequence encoding the recombinant N-terminal GST-tagged LANCL1 protein 1-42amino acid region for raising antibodies:
ATGTCCCCTATACTAGGTTATTGGAAAATTAAGGGCCTTGTGCAACCCACTCGACTTCTTTTGGAATATCTTGAAGAAAAATA
TGAAGAGCATTTGTATGAGCGCGATGAAGGTGATAAATGGCGAAACAAAAAGTTTGAATTGGGTTTGGAGTTTCCCAATCTTC
CTTATTATATTGATGGTGATGTTAAATTAACACAGTCTATGGCCATCATACGTTATATAGCTGACAAGCACAACATGTTGGGT
GGTTGTCCAAAAGAGCGTGCAGAGATTTCAATGCTTGAAGGAGCGGTTTTGGATATTAGATACGGTGTTTCGAGAATTGCATA
TAGTAAAGACTTTGAAACTCTCAAAGTTGATTTTCTTAGCAAGCTACCTGAAATGCTGAAAATGTTCGAAGATCGTTTATGTC
ATAAAACATATTTAAATGGTGATCATGTAACCCATCCTGACTTCATGTTGTATGACGCTCTTGATGTTGTTTTATACATGGAC
CCAATGTGCCTGGATGCGTTCCCAAAATTAGTTTGTTTTAAAAAACGTATTGAAGCTATCCCACAAATTGATAAGTACTTGAA
ATCCAGCAAGTATATAGCATGGCCTTTGCAGGGCTGGCAAGCCACGTTTGGTGGTGGCGACCATCCTCCAAAATCGGATCTGG
TTCCGCGTGGATCCATGGCTCAAAGGGCCTTCCCGAATCCTTATGCTGATTATAACAAATCCCTGGCCGAAGGCTACTTTGAT
GCTGCCGGGAGGCTGACTCCTGAGTTCAGCCAGAGACTGACCAATAAGATTCGGGAGTAG SEQ ID NO: 12: amino acid sequence for the 1-47amino acid peptide that was targeted by antibody manufactured by Novus Biologicals (NBP1-81796):
MAQRAFPNPYADYNKSLAEGYFDAAGRLTPEFSQRLTNKIRELLQQM SEQ ID NO: 13: amino acid sequence for the 1-58amino acid peptide that was targeted by antibody manufactured by Abnova (H00010314-A01):
MAQRAFPNPYADYNKSLAEGYFDAAGRLTPEFSQRLTNKIRELLQQMERGLKSADPRD -continued

| SEQUENCES |
|---|
| SEQ ID NO: 14: amino acid sequence for the 1-47amino acid peptide that was targeted by antibody manufactured by Sigma-Aldrich (HPA034994): MAQRAFPNPYADYNKSLAEGYFDAAGRLTPEFSQRLTNKIRELLQQM |

It should be understood that the examples and embodiments described herein are for illustrative purposes only and that various modifications or changes in light thereof will be suggested to persons skilled in the art and are to be included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

EXEMPLIFIED EMBODIMENTS

Embodiment 1. A method of inhibiting cancer cell proliferation in a subject, comprising administering to the subject an antibody that specifically binds to LANCL1, wherein the antibody binds to SEQ ID NO: 8, 9 10, 11, 12, 13 or a sequence having at least 80% sequence identity to SEQ ID NO: 8, 9 10, or 11, 12, 13.

Embodiment 2. The method of embodiment 1, wherein the cancer cell is a tumor initiating cell.

Embodiment 3. The method of embodiment 2, wherein the cancer cell is a hepatocellular carcinoma cell.

Embodiment 4. The method of embodiment 1, wherein the antibody is a monoclonal antibody.

Embodiment 5. The method of embodiment 1, wherein the antibody is a polyclonal antibody.

Embodiment 6. The method of embodiment 1, wherein the antibody is selected from a chimeric antibody, a single chain antibody, and a single chain fragment variable (scFv) antibody.

Embodiment 7. The method of embodiment 1, wherein the antibody is an Abnova H00010314-A01 antibody, Sigma-Aldrich HPA034994 antibody, or a Novus Biologicals NBP1-81796 antibody.

Embodiment 8. The method of embodiment 1, wherein the antibody is conjugated to a label.

Embodiment 9. The method of embodiment 8, wherein the label is selected from an enzyme label, a radioisotope, a fluorescent label, a drug molecule label, a bioluminescent label, and an antibody.

Embodiment 10. The method of embodiment 1, wherein the antibody is an Abnova H00010314-A01 antibody, Sigma-Aldrich HPA034994 antibody, a Novus Biologicals NBP1-81796 antibody, or any combination thereof.

REFERENCES

1. Yi S Y, Hao Y B, Nan K J, Fan T L. Cancer stem cells niche: a target for novel cancer therapeutics. Cancer Treat Rev 2013; 39:290-296.
2. Visvader J E, Lindeman G J. Cancer stem cells in solid tumours: accumulating evidence and unresolved questions. Nat Rev Cancer 2008; 8:755-768.
3. Tirino V, Desiderio V, Paino F, De Rosa A, Papaccio F, La Noce M, Laino L, et al. Cancer stem cells in solid tumors: an overview and new approaches for their isolation and characterization. FASEB J 2013; 27:13-24.
4. Sze K M, Ho D W, Chiu Y T, Tsui Y M, Chan L K, Lee J M, Chok K S, et al. Hepatitis B Virus-Telomerase Reverse Transcriptase Promoter Integration Harnesses Host ELF4, Resulting in Telomerase Reverse Transcriptase Gene Transcription in Hepatocellular Carcinoma. Hepatology 2021; 73:23-40.
5. Huang C, Chen M, Pang D, Bi D, Zou Y, Xia X, Yang W, et al. Developmental and activity-dependent expression of LanCL1 confers antioxidant activity required for neuronal survival. Dev Cell 2014; 30:479-487.
6. Wang J, Xiao Q, Chen X, Tong S, Sun J, Lv R, Wang S, et al. LanCL1 protects prostate cancer cells from oxidative stress via suppression of JNK pathway. Cell Death Dis 2018; 9:197.
7. Lee T K, Castilho A, Cheung V C, Tang K H, Ma S, Ng T O. CD24(+) liver tumor-initiating cells drive self-renewal and tumor initiation through STAT3-mediated NANOG regulation. Cell Stem Cell 2011; 9:50-63.
8. Ma S, Chan K W, Hu L, Lee T K, Wo J Y, Ng T O, Zheng B J, et al. Identification and characterization of tumorigenic liver cancer stem/progenitor cells. Gastroenterology 2007; 132:2542-2556.
9. Cui C P, Wong C C, Kai A K, Ho D W, Lau E Y, Tsui Y M, Chan L K, et al. SENP1 promotes hypoxia-induced cancer stemness by HIF-1alpha deSUMOylation and SENP1/HIF-1alpha positive feedback loop. Gut 2017; 66:2149-2159.

We claim:

1. A method of inhibiting cancer cell proliferation in a subject, comprising administering to the subject an antibody that specifically binds to LANCL1, wherein the antibody binds to SEQ ID NO: 8, 12, or 13, wherein the cancer cell is a liver tumor initiating cell, wherein the cancer cell is a hepatocellular carcinoma cell, wherein the antibody is an Abnova H00010314-A01 antibody, Sigma-Aldrich HPA034994 antibody, or a Novus Biologicals NBP1-81796 antibody.

2. The method of claim 1, wherein the antibody is conjugated to a label.

3. The method of claim 2, wherein the label is selected from an enzyme label, a radioisotope, a fluorescent label, a drug molecule label, a bioluminescent label, and an antibody.

* * * * *